(12) United States Patent
Han et al.

(10) Patent No.: US 10,322,127 B2
(45) Date of Patent: *Jun. 18, 2019

(54) METHODS AND KITS TO PREDICT THERAPEUTIC OUTCOME OF BTK INHIBITORS

(71) Applicant: THE TRANSLATIONAL GENOMICS RESEARCH INSTITUTE, Phoenix, AZ (US)

(72) Inventors: Haiyong Han, Chandler, AZ (US); Daniel Von Hoff, Scottsdale, AZ (US); Caroline H. Diep, Minneapolis, MN (US); Hongwei Yin, Scottsdale, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 64 days.

This patent is subject to a terminal disclaimer.

(21) Appl. No.: 15/186,636

(22) Filed: Jun. 20, 2016

(65) Prior Publication Data

US 2016/0346285 A1    Dec. 1, 2016

Related U.S. Application Data

(63) Continuation of application No. 13/642,430, filed as application No. PCT/US2011/033136 on Apr. 19, 2011, now Pat. No. 9,371,567.

(60) Provisional application No. 61/325,683, filed on Apr. 19, 2010.

(51) Int. Cl.
| | | |
|---|---|---|
| A61K 9/00 | (2006.01) | |
| A61K 31/519 | (2006.01) | |
| C12Q 1/6886 | (2018.01) | |

(52) U.S. Cl.
CPC .......... *A61K 31/519* (2013.01); *A61K 9/0019* (2013.01); *A61K 9/0053* (2013.01); *C12Q 1/6886* (2013.01); *C12Q 2600/106* (2013.01); *C12Q 2600/136* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2008/0139582 A1* 6/2008 Honigberg ............. A61K 31/00
514/262.1

OTHER PUBLICATIONS

Diep (Experimental and Molecular Therapeutics Proceedings: AACR 101st Annual Meeting 2010 Apr. 17-21, 2010, Washington DC Published Apr. 15, 2010).*
Wilentz (Cancer Research 60 2002-2006 Apr. 1, 2000).*

* cited by examiner

*Primary Examiner* — Amanda Haney
(74) *Attorney, Agent, or Firm* — Rodney J. Fuller; Booth Udall Fuller, PLC

(57) ABSTRACT

Methods of tests that assess the expression of DPC4 (SMAD4) to identify subjects with pancreatic cancer that are likely or unlikely to respond to treatment with BTK inhibitors; methods of treating subjects based on identification of the subjects as likely to respond to treatment with BTK inhibitors; therapeutic targets for cancers, particularly cancers with inactivated DPC4 gene or protein; methods of screening of new therapeutic agents using the target; pharmaceutical composition comprising BTK inhibitors, such as PCI-32765 or derivatives thereof, for cancer treatment; and kits that facilitate the performance of the methods are disclosed.

20 Claims, 10 Drawing Sheets
Specification includes a Sequence Listing.

SEQUENCE LISTING

```
<160> NUMBER OF SEQ ID NOS: 2

<210> SEQ ID NO 1
<211> LENGTH: 8789
<212> TYPE: DNA
<213> ORGANISM: Homo sapiens

<400> SEQUENCE: 1
atgctcagtg gcttctcgac aagttggcag caacaacacg gccctggtcg tcgtcgccgc      60
tgcggtaacg gagcggtttg ggtggcggag cctgcgttcg cgccttcccg ctctcctcgg     120
gaggcccttc ctgctctccc ctaggctccg cggccgccca gggggtggga gcgggtgagg     180
ggagccaggc gcccagcgag agaggccccc cgccgcaggg cggcccggga gctcgaggcg     240
gtccggcccg cgcgggcagc ggcgcggcgc tgaggagggg cggcctggcc gggacgcctc     300
ggggcggggg ccgaggagct ctccgggccg ccggggaaag ctacgggccc ggtgcgtccg     360
cggaccagca gcgcgggaga gcggactccc ctcgccaccg cccgagccca ggttatcctg     420
aatacatgtc taacaatttt ccttgcaacg ttagctgttg tttttcactg tttccaaagg     480
atcaaaattg cttcagaaat tggagacata tttgatttaa aaggaaaaac ttgaacaaat     540
ggacaatatg tctattacga atacaccaac aagtaatgat gcctgtctga gcattgtgca     600
tagtttgatg tgccatagac aaggtggaga gagtgaaaca tttgcaaaaa gagcaattga     660
aagtttggta aagaagctga aggagaaaaa agatgaattg gattctttaa taacagctat     720
aactacaaat ggagctcatc ctagtaaatg tgttaccata cagagaacat tggatgggag     780
gcttcaggtg gctggtcgga aaggatttcc tcatgtgatc tatgcccgtc tctggaggtg     840
```

```
gcctgatctt cacaaaaatg aactaaaaca tgttaaatat tgtcagtatg cgtttgactt      900
aaaatgtgat agtgtctgtg tgaatccata tcactacgaa cgagttgtat cacctggaat      960
tgatctctca ggattaacac tgcagagtaa tgctccatca agtatgatgg tgaaggatga     1020
atatgtgcat gactttgagg acagccatc gttgtccact gaaggacatt caattcaaac     1080
catccagcat ccaccaagta atcgtgcatc gacagagaca tacagcaccc cagctctgtt     1140
agccccatct gagtctaatg ctaccagcac tgccaacttt cccaacattc tgtggcttc      1200
cacaagtcag cctgccagta tactggggggg cagccatagt gaaggactgt tgcagatagc    1260
atcagggcct cagccaggac agcagcagaa tggatttact ggtcagccag ctacttacca    1320
tcataacagc actaccacct ggactggaag taggactgca ccatacacac ctaatttgcc    1380
tcaccaccaa aacggccatc ttcagcacca cccgcctatg ccgccccatc ccggacatta    1440
ctggcctgtt cacaatgagc ttgcattcca gcctcccatt tccaatcatc ctgctcctga    1500
gtattggtgt tccattgctt actttgaaat ggatgttcag gtaggagaga catttaaggt    1560
tccttcaagc tgccctattg ttactgttga tggatacgtg gaccctctg gaggagatcg      1620
cttttgtttg ggtcaactct ccaatgtcca caggacagaa gccattgaga gagcaaggtt    1680
gcacataggc aaaggtgtgc agttggaatg taaaggtgaa ggtgatgttt gggtcaggtg    1740
ccttagtgac cacgcggtct ttgtacagag ttactactta gacagagaag ctgggcgtgc    1800
acctggagat gctgttcata agatctaccc aagtgcatat ataaaggtct ttgatttgcg    1860
tcagtgtcat cgacagatgc agcagcaggc ggctactgca caagctgcag cagctgccca    1920
ggcagcagcc gtggcaggaa acatccctgg cccaggatca gtaggtggaa tagctccagc    1980
tatcagtctg tcagctgctg ctggaattgg tgttgatgac cttcgtcgct tatgcatact    2040
caggatgagt tttgtgaaag gctggggacc ggattaccca agacagagca tcaaagaaac    2100
accttgctgg attgaaattc acttacaccg ggccctccag ctcctagacg aagtacttca    2160
taccatgccg attgcagacc cacaaccttt agactgaggt cttttaccgt tggggccctt    2220
aaccttatca ggatggtgga ctacaaaata caatcctgtt tataatctga agatatattt    2280
cactttttgtt ctgctttatc ttttcataaa ggggttgaaaa tgtgtttgct gccttgctcc    2340
tagcagacag aaactggatt aaaacaattt ttttttttcct cttcagaact tgtcaggcat    2400
ggctcagagc ttgaagatta ggagaaacac attcttatta attcttcacc tgttatgtat    2460
gaaggaatca ttccagtgct agaaaattta gcccctttaaa acgtcttaga gccttttatc    2520
tgcagaacat cgatatgtat atcattctac agaataatcc agtattgctg attttaaagg    2580
cagagaagtt ctcaaagtta attcacctat gttatttgt gtacaagttg ttattgttga     2640
acatacttca aaaataatgt gccatgtggg tgagttaatt ttaccaagag taactttact    2700
ctgtgtttaa aaagtaagtt aataatgtat tgtaatcttt catccaaaat atttttgca     2760
agttatatta gtgaagatgg tttcaattca gattgtcttg caacttcagt tttatttttg    2820
ccaaggcaaa aaactcttaa tctgtgtgta tattgagaat cccttaaaat taccagacaa    2880
aaaaatttaa aattacgttt gttattccta gtggatgact gttgatgaag tatactttc     2940
ccctgttaaa cagtagttgt attcttctgt atttctaggc acaaggttgg ttgctaagaa    3000
gcctataaga ggaatttctt ttccttcatt catagggaaa ggttttgtat tttttaaaac    3060
actaaaagca gcgtcactct acctaatgtc tcactgttct gcaaaggtgg caatgcttaa    3120
actaaataat gaataaactg aatatttttgg aaactgctaa attctatgtt aaatactgtg    3180
cagaataatg gaaacattac agttcataat aggtagtttg gatatttttg tacttgattt    3240
```

```
gatgtgactt tttttggtat aatgtttaaa tcatgtatgt tatgatattg tttaaaattc    3300
agttttgta  tcttggggca  agactgcaaa ctttttata  tcttttggtt attctaagcc   3360
ctttgccatc aatgatcata tcaattggca gtgactttgt atagagaatt taagtagaaa    3420
agttgcagat gtattgactg taccacagac acaatatgta tgcttttac  ctagctggta    3480
gcataaataa aactgaatct caacatacaa agttgaattc taggtttgat ttttaagatt    3540
tttttttct  tttgcactt  tgagtccaat ctcagtgatg aggtaccttc tactaaatga    3600
caggcaacag ccagttctat tgggcagctt tgtttttttc cctcacactc taccgggact    3660
tccccatgga cattgtgtat catgtgtaga gttggttttt ttttttttta attttattt     3720
tactatagca gaaatagacc tgattatcta caagatgata aatagattgt ctacaggata    3780
aatagtatga aataaaatca aggattatct ttcagatgtg tttactttg  cctggagaac    3840
ttttagctat agaaacactt gtgtgatgat agtcctcctt atatcacctg aatgaacac     3900
agcttctact gccttgctca gaaggtcttt taaatagacc atcctagaaa ccactgagtt    3960
tgcttatttc tgtgatttaa acatagatct tgatccaagc tacatgactt ttgtctttaa    4020
ataacttatc taccacctca tttgtactct tgattactta caattctttt cagtaaacac    4080
ctaattttct tctgtaaaag tttggtgatt taagtttat  tggcagtttt ataaaaagac    4140
atcttctcta gaaattgcta actttaggtc catttttactg tgaatgagga ataggagtga   4200
gttttagaat aacagatttt taaaaatcca gatgatttga ttaaaaccttt aatcatacat   4260
tgacataatt cattgcttct ttttttgag  atatggagtc ttgctgtgtt gcccaggcag    4320
gagtgcagtg gtatgatctc agctcactgc aacctctgcc tcccgggttc aactgattct    4380
cctgcctcag cctccctggt agctaggatt acaggtgccc gccaccatgc ctggctaact    4440
tttgtagttt tagtagagac ggggttttgc ctgttggcca ggctggtctt gaactcctga    4500
cctcaagtga tccatccacc ttggcctccc aaagtgctgg gattacgggc gtgagccact    4560
gtccctggcc tcattgttcc cttttctact ttaaggaaag ttttcatgtt taatcatctg    4620
gggaaagtat gtgaaaaata tttgttaaga agtatctctt tggagccaag ccacctgtct    4680
tggtttcttt ctactaagag ccataaagta tagaaatact tctagttgtt aagtgcttat    4740
atttgtacct agatttagtc acacgctttt gagaaaacat ctagtatgtt atgatcagct    4800
attcctgaga gcttggttgt taatctatat ttctatttct tagtggtagt catctttgat    4860
gaataagact aaagattctc acaggtttaa aattttatgt ctactttaag ggtaaaatta    4920
tgaggttatg gttctgggtg ggttttctct agctaattca tatctcaaag agtctcaaaa    4980
tgttgaattt cagtgcaagc tgaatgagag atgagccatg tacacccacc gtaagacctc    5040
attccatgtt tgtccagtgc ctttcagtgc attatcaaag ggaatccttc atggtgttgc    5100
ctttattttc cggggagtag atcgtgggat atagtctatc tcatttttaa tagtttaccg    5160
cccctggtat acaaagataa tgacaataaa tcactgccat ataaccttgc ttttccaga    5220
aacatggctg ttttgtattg ctgtaaccac taaataggtt gcctatacca ttcctcctgt    5280
gaacagtgca gatttacagg ttgcatggtc tggcttaagg agagccatac ttgagacatg    5340
tgagtaaact gaactcatat tagctgtgct gcatttcaga cttaaaatcc attttttgtgg   5400
ggcagggtgt ggtgtgtaaa ggggggtgtt tgtaatacaa gttgaaggca aaataaaatg    5460
tcctgtctcc cagatgatat acatcttatt attttttaaag tttattgcta attgtaggaa   5520
ggtgagttgc aggtatcttt gactatggtc atctgggaa  ggaaaatttt acattttact    5580
```

```
attaatgctc cttaagtgtc tatggaggtt aaagaataaa atggtaaatg tttctgtgcc   5640
tggtttgatg gtaactggtt aatagttact caccatttta tgcagagtca cattagttca   5700
caccctttct gagagccttt tgggagaagc agttttattc tctgagtgga acagagttct   5760
ttttgttgat aatttctagt ttgctcccctt cgttattgcc aactttactg gcattttatt   5820
taatgatagc agattgggaa aatggcaaat ttaggttacg gaggtaaatg agtatatgaa   5880
agcaattacc tctaaagcca gttaacaatt attttgtagg tggggtacac tcagcttaaa   5940
gtaatgcatt ttttttttccc gtaaaggcag aatccatctt gttgcagata gctatctaaa   6000
taatctcata tcctcttttg caaagactac agagaatagg ctatgacaat cttgttcaag   6060
cctttccatt tttttccctg ataactaagt aatttctttg aacataccaa gaagtatgta   6120
aaaagtccat ggccttattc atccacaaag tggcatccta ggcccagcct tatccctagc   6180
agttgtccca gtgctgctag gttgcttatc ttgtttatct ggaatcactg tggagtgaaa   6240
ttttccacat catccagaat tgccttattt aagaagtaaa acgttttaat ttttagcctt   6300
tttttggtgg agttatttaa tatgtatatc agaggatata ctagatggta acatttcttt   6360
ctgtgcttgg ctatctttgt ggacttcagg ggcttctaaa acagacagga ctgtgttgcc   6420
tttactaaat ggtctgagac agctatggtt ttgaattttt agttttttttt ttttaaccca   6480 cttcccctcc tggtctcttc cctctctgat aattaccatt catatgtgag tgttagtgtg   6540 cctccttttta gcattttctt cttctctttc tgattcttca tttctgactg cctaggcaag   6600
gaaaccagat aaccaaactt actagaacgt tctttaaaac acaagtacaa actctgggac   6660
aggacccaag acactttcct gtgaagtgct gaaaaagacc tcattgtatt ggcatttgat   6720
atcagtttga tgtagcttag agtgcttcct gattcttgct gagtttcagg tagttgagat   6780
agagagaagt gagtcatatt catattttcc cccttagaat aatattttga aaggtttcat   6840
tgcttccact tgaatgctgc tcttacaaaa actggggtta caagggttac taaattagca   6900
tcagtagcca gaggcaatac cgttgtctgg aggacaccag caaacaacac acaacaaagc   6960
aaaacaaacc ttgggaaact aaggccattt gttttgtttt ggtgtcccct ttgaagccct   7020
gccttctggc cttactcctg tacagatatt tttgacctat aggtgccttt atgagaattg   7080
agggtctgac atcctgcccc aaggagtagc taaagtaatt gctagtgttt tcagggattt   7140
taacatcaga ctggaatgaa tgaatgaaac ttttgtcct ttttttttct gtttttttt   7200 ttctaatgta gtaaggacta aggaaaacct ttggtgaaga caatcatttc tctctgttga   7260
tgtggatact tttcacaccg tttatttaaa tgctttctca ataggtccag agccagtgtt   7320
cttgttcaac ctgaaagtaa tggctctggg ttgggccaga cagttgcact ctctagtttg   7380
ccctctgcca caaatttgat gtgtgacctt tgggcaagtc atttatcttc tctgggcctt   7440
agttgcctca tctgtaaaat gagggagttg gagtagatta attattccag ctctgaaatt   7500
ctaagtgacc ttggctacct tgcagcagtt ttggatttct tccttatctt tgttctgctg   7560
tttgaggggg cttttacttt atttccatgt tattcaaagg agactaggct tgatatttta   7620
ttactgttct tttatggaca aaaggttaca tagtatgccc ttaagactta attttaacca   7680
aaggcctagc accaccttag gggctgcaat aaacacttaa cgcgcgtgcg cacgcgcgcg   7740
cgcacacaca cacacacaca cacacacaca cacaggtcag agtttaaggc tttcgagtca   7800
tgacattcta gcttttgaat tgcgtgcaca cacacacgca cgcacacact ctggtcagag   7860
tttattaagg ctttcgagtc atgacattat agcttttgag ttggtgtgtg tgacaccacc   7920
ctcctaagtg gtgtgtgctt gtaattttttt ttttcagtga aaatggattg aaaacctgtt   7980
```

```
gttaatgctt agtgatatta tgctcaaaac aaggaaattc ccttgaaccg tgtcaattaa   8040
actggtttat atgactcaag aaaacaatac cagtagatga ttattaactt tattcttggc   8100 tcttttagg tccatttga ttaagtgact tttggctgga tcattcagag ctctcttcta    8160 gcctacccctt ggatgagtac aattaatgaa attcatattt tcaaggacct gggagccttc  8220
cttggggctg ggttgagggt ggggggttgg ggagtcctgg tagaggccag ctttgtggta   8280
gctggagagg aagggatgaa accagctgct gttgcaaagg ctgcttgtca ttgatagaag   8340
gactcacggg cttggattga ttaagactaa acatggagtt ggcaaacttt cttcaagtat   8400
tgagttctgt tcaatgcatt ggacatgtga tttaagggaa aagtgtgaat gcttatagat   8460
gatgaaaacc tggtgggctg cagagcccag tttagaagaa gtgagttggg ggttggggac   8520
agatttggtg gtggtatttc ccaactgttt cctcccctaa attcagagga atgcagctat   8580
gccagaagcc agagaagagc cactcgtagc ttctgctttg gggacaactg gtcagttgaa   8640
agtcccagga gttcctttgt ggctttctgt atacttttgc ctggttaaag tctgtggcta   8700
aaaaatagtc gaacctttct tgagaactct gtaacaaagt atgttttga ttaaaagaga    8760 aagccaacta aaaaaaaaaa aaaaaaaaa                                     8789

<210> SEQ ID NO 2
<211> LENGTH: 552
<212> TYPE: PRT
<213> ORGANISM: Homo sapiens

<400> SEQUENCE: 2

Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
    130                 135                 140

Gly Leu Thr Leu Gln Ser Asn Ala Pro Ser Ser Met Met Val Lys Asp
145                 150                 155                 160

Glu Tyr Val His Asp Phe Glu Gly Gln Pro Ser Leu Ser Thr Glu Gly
                165                 170                 175

His Ser Ile Gln Thr Ile Gln His Pro Pro Ser Asn Arg Ala Ser Thr
            180                 185                 190

Glu Thr Tyr Ser Thr Pro Ala Leu Leu Ala Pro Ser Glu Ser Asn Ala
        195                 200                 205

Thr Ser Thr Ala Asn Phe Pro Asn Ile Pro Val Ala Ser Thr Ser Gln
    210                 215                 220
```

-continued

```
Pro Ala Ser Ile Leu Gly Gly Ser His Ser Glu Gly Leu Leu Gln Ile
225                 230                 235                 240

Ala Ser Gly Pro Gln Pro Gly Gln Gln Gln Asn Gly Phe Thr Gly Gln
            245                 250                 255

Pro Ala Thr Tyr His His Asn Ser Thr Thr Thr Trp Thr Gly Ser Arg
            260                 265                 270

Thr Ala Pro Tyr Thr Pro Asn Leu Pro His His Gln Asn Gly His Leu
            275                 280                 285

Gln His His Pro Pro Met Pro Pro His Pro Gly His Tyr Trp Pro Val
        290                 295                 300

His Asn Glu Leu Ala Phe Gln Pro Pro Ile Ser Asn His Pro Ala Pro
305                 310                 315                 320

Glu Tyr Trp Cys Ser Ile Ala Tyr Phe Glu Met Asp Val Gln Val Gly
                325                 330                 335

Glu Thr Phe Lys Val Pro Ser Ser Cys Pro Ile Val Thr Val Asp Gly
            340                 345                 350

Tyr Val Asp Pro Ser Gly Gly Asp Arg Phe Cys Leu Gly Gln Leu Ser
            355                 360                 365

Asn Val His Arg Thr Glu Ala Ile Glu Arg Ala Arg Leu His Ile Gly
370                 375                 380

Lys Gly Val Gln Leu Glu Cys Lys Gly Glu Gly Asp Val Trp Val Arg
385                 390                 395                 400

Cys Leu Ser Asp His Ala Val Phe Val Gln Ser Tyr Tyr Leu Asp Arg
                405                 410                 415

Glu Ala Gly Arg Ala Pro Gly Asp Ala Val His Lys Ile Tyr Pro Ser
            420                 425                 430

Ala Tyr Ile Lys Val Phe Asp Leu Arg Gln Cys His Arg Gln Met Gln
            435                 440                 445

Gln Gln Ala Ala Thr Ala Gln Ala Ala Ala Ala Gln Ala Ala Ala
    450                 455                 460

Val Ala Gly Asn Ile Pro Gly Pro Gly Ser Val Gly Gly Ile Ala Pro
465                 470                 475                 480

Ala Ile Ser Leu Ser Ala Ala Gly Ile Gly Val Asp Asp Leu Arg
            485                 490                 495

Arg Leu Cys Ile Leu Arg Met Ser Phe Val Lys Gly Trp Gly Pro Asp
            500                 505                 510

Tyr Pro Arg Gln Ser Ile Lys Glu Thr Pro Cys Trp Ile Glu Ile His
        515                 520                 525

Leu His Arg Ala Leu Gln Leu Leu Asp Glu Val Leu His Thr Met Pro
    530                 535                 540

Ile Ala Asp Pro Gln Pro Leu Asp
545                 550
```

METHODS AND KITS TO PREDICT THERAPEUTIC OUTCOME OF BTK INHIBITORS

CROSS REFERENCE TO RELATED APPLICATIONS

This application is a continuation of U.S. patent application Ser. No. 13/642,430, filed on Jun. 14, 2013, which is a U.S. National Stage Application filed under 35 U.S.C. § 371 from PCT Patent Application No. PCT/US2011/033136, filed on Apr. 19, 2011, which claims priority to U.S. provisional application No. 61/325,683, filed on Apr. 19, 2010, all of which are hereby incorporated by reference in its entirety.

STATEMENT REGARDING FEDERALLY SPONSORED RESEARCH

This invention was made with government support under CA109552 awarded by the National Institutes of Health. The government has certain rights in this invention.

FIELD OF THE INVENTION

This invention relates to the identification of BTK (Bruton tyrosine kinase) as a therapeutic target for various cancers, particularly for cancers associated with the inactivation of tumor suppressing gene DPC4 and also as a drug screening target. The present invention also relates to the selection of cancer patients most likely to respond or not to respond to one or more tyrosine kinase inhibitors.

BACKGROUND OF THE INVENTION

While FDA approved drugs are approved as safe and effective for the population as a whole, the majority of drugs do not work in all patients to which they are administered. However at present, many drugs are administered to patients without a prediction of whether or not the drug will be effective in a particular patient. This results in higher than necessary health care costs and risk to patients. There is a need in the art to develop new patient selection methods that will match patients to the correct treatment.

It has been known that one of the most common types of genetic alterations in cancer is the loss-of-function mutations in tumor-suppressor genes. The DPC4 gene (Deleted in Pancreatic Cancer locus 4), a tumor-suppressor gene located at 18q21.1, has been shown to mediate the effects of TGF-superfamily signaling, resulting in downstream growth inhibition. However, DPC4 is inactivated in approximately 55% of pancreatic adenocarcinomas. Pancreatic cancer is the fifth most common cause of tumor-related deaths in the industrialized world. Fewer than 10% to 20% of patients are candidates for surgery at the time of presentation, and <20% of patients who undergo curative resection are alive after 5 years. Despite recent progress, there is no modality for early detection of pancreatic cancer. In addition, mutations in DPC4 also have been identified in other tumor types, including bladder (12-35%), lung (24-65%), prostate (19-45%), ovarian (27-67%) carcinomas, 10% of proximal and 55% of distal bile duct carcinomas. Therefore there is a need to identify potential lethal targets against the deficiency of the DPC4 gene, so that the lethal targets may be used for developing treatments for cancers, particularly for cancers with inactivated DPC4 gene or gene product.

SUMMARY OF THE INVENTION

Briefly, therefore, one aspect of the present invention provides a method for identifying a modulator of BTK. The method comprises (a) contacting a cancer cell overexpressing BTK with the modulator, wherein the cancer cell comprises inactivated DPC4 gene or gene product thereof; and (b) testing one or more cancer cell responses to the modulator, wherein the cancer cell response is chosen from cancer cell count, expansion, migration, metastasis, apoptosis; wherein the cancer cell response is compared relative to a control.

Yet another aspect of the present invention provides a method of treating cancer patients, comprising administering to a patient a therapeutically effective amount of a pharmaceutical composition comprising PCI-32765.

Still another aspect of the present invention provides a kit comprising a pharmaceutical composition comprising PCI-32765 or its derivatives for treating cancer.

Other aspects and iterations of the invention are described in more detail below.

The present invention provides among other things, a personalized medicine based method that allows the selection of cancer patients most likely to respond or not to respond to one or more tyrosine kinase inhibitors.

It is an object of the invention to identify tumors that are resistant or sensitive to BTK inhibitors.

It is an object of the invention to stage patients with regard to treatment with BTK inhibitors, assuring that the treatment is more likely to be given to those patients with the best chance of responding to it.

It is an object of the invention to prevent health care providers to select other treatments for patients for whom BTK inhibitors are unlikely to work.

It is an object of the invention to provide a test that allows the prediction of whether or not a pancreatic cancer patient will respond to a BTK inhibitor.

It is an object of the invention to classify subjects into cohorts that include individuals likely to respond and individuals to a BTK inhibitor or individuals not likely to respond to a BTK inhibitor.

It is an object of the invention to treat a subject on the basis of a result that indicates whether or not a patient will respond to a BTK inhibitor.

It is an object of the invention to provide kits that facilitate the identification of a patient as likely to respond to a BTK inhibitor or unlikely to respond to a BTK inhibitor.

The above and other objects may be achieved through the use of methods involving receiving a sample from a subject and isolating RNA from the sample, adding a first reagent capable of specific binding to a marker that includes SEQ ID NO. 1, to a mixture comprising the sample and subjecting the mixture to conditions that allow detection of the binding of the first reagent to the marker. The subject is suspected of having pancreatic or colon cancer. The cohort includes two or more individuals likely to respond to treatment with a Btk inhibitor. The first reagent may comprise a first oligonucleotide. The method may further comprise adding reverse transcriptase and subjecting the mixture to conditions that comprise allowing the formation of a DNA template comprising the marker. The method may further comprise adding a second oligonucleotide and a third oligonucleotide to the mixture. The second oligonucleotide and the third oligonucleotide bind to opposite strands of the DNA template. For example, if the second oligonucleotide binds to the 5'→3' strand, then the third oligonucleotide binds to the 3'→5' strand. The method may further comprise adding a fourth oligonucleotide to the mixture. The fourth oligonucleotide binds to the DNA template between the sequences to which the second oligonucleotide and the third oligonucleotide are capable of binding. The fourth oligonucleotide may comprise a label. The label may be any label including a fluorescent label such as FAM, dR110, 5-FAM, 6FAM, dR6G, JOE, HEX, VIC, TET, dTAMRA, TAMRA, NED, dROX, PET, BHQ, Gold540, or LIZ. Alternatively, the conditions may comprise DNA sequencing wherein cohort further comprises two or more individuals with a mutation in SEQ ID NO: 1. The first reagent may comprise a first antibody. The first antibody may comprise a first label such as a fluorescent compound, an enzyme, or a ligand. Alternatively, the method may further comprise adding a second antibody to the mixture wherein the second antibody is capable of binding to the first antibody. The first reagent may be affixed to a substrate. The sample may be any sample including a sample The second antibody may comprise a second label such as a fluorescent compound, an enzyme, or a ligand. The ligand may be any ligand including biotin or streptavidin. The first reagent may be affixed to a substrate. The sample may be any sample including a sample comprising serum (such as whole blood) or a sample comprising one or more cells such as a pancreas biopsy or metastatic tumor. The method may also include collecting the sample from the subject. The BTK inhibitor may be any BTK inhibitor including PCI-32765.

The above and other objects may be achieved through the use of kits comprising a first reagent capable of specific binding to a marker that includes SEQ ID NO: 1 and an indication of a result that signifies classification of the subject into a cohort, wherein the cohort comprises two or more individuals likely to respond to treatment with a Btk inhibitor. The first reagent may comprise a first oligonucleotide. The kit may further comprise a second oligonucleotide and a third oligonucleotide wherein the second oligonucleotide and the third oligonucleotide are capable of binding to opposite strands of a DNA construct comprising the reverse transcription product of the marker. For example, if the second oligonucleotide binds to the 5'→3' strand, then the third oligonucleotide binds to the 3'→5' strand. The kit may further comprise a fourth oligonucleotide capable of binding to a sequence between the sequences to which the second oligonucleotide and the third oligonucleotide are capable of binding. The fourth oligonucleotide may comprise a label, including a fluorescent label such as FAM, dR110, 5-FAM, 6FAM, dR6G, JOE, HEX, VIC, TET, dTAMRA, TAMRA, NED, dROX, PET, or LIZ. The kit may also comprise an enzyme such as a DNA polymerase, (including, for example, a thermostable DNA polymerase) or a reverse transcriptase. Alternatively, the first reagent may comprise a first antibody. The first antibody may comprise a first label. The first label may be any label such as a fluorescent compound, enzyme, or ligand. The kit may further comprise a second antibody capable of hybridizing to the first antibody. The second antibody may comprise a second label such as a fluorescent compound, enzyme, or ligand. The ligand may be any ligand including streptavidin or biotin. Alternatively, the first reagent may be affixed to a substrate. The kit may further comprise a device to be used in collecting a sample. The result may comprise a ⊗ Ct value. The result may alternatively comprise a nucleic acid sequence. The indication may comprise a positive control. Alternatively, the indication may comprise a writing that may be physically included in the kit, may be made available via a website, may comprise an amplification plot, or may comprise a photograph. Alternatively, the indication may comprise software configured to detect the result as input and classification of the subject into the cohort as output. The software may be incorporated into any machine including a machine configured to detect fluorescence. The BTK inhibitor may be any BTK inhibitor such as PCI-32765.

The above and other objects may be achieved through the use of methods involving receiving a sample from a subject and isolating RNA from the sample, adding a first reagent capable of specific binding to a marker that includes SEQ ID NO: 1, to a mixture; subjecting the mixture to conditions that allow detection of the binding of the first reagent to the sequence, and treating with a BTK inhibitor based upon a result indicated by the binding of the first reagent to the sequence. The subject is suspected of having pancreatic or colon cancer. The cohort comprises two or more individuals likely to respond to treatment with a BTK inhibitor. The first reagent may comprise a first oligonucleotide. The method may further comprise adding reverse transcriptase and subjecting the mixture to conditions that comprise allowing the formation of a DNA template comprising the marker. The method may further comprise adding a second oligonucleotide and a third oligonucleotide to the mixture. The second oligonucleotide and the third oligonucleotide bind to opposite strands of the DNA template. For example, if the second oligonucleotide binds to the 5'→3' strand, then the third oligonucleotide binds to the 3'→5' strand. The method may further comprise adding a fourth oligonucleotide to the mixture. The fourth oligonucleotide binds to the DNA template between the sequences to which the second oligonucleotide and the third oligonucleotide are capable of binding. The fourth oligonucleotide may comprise a label. The label may be any label including a fluorescent label such as FAM, dR110, 5-FAM, 6FAM, dR6G, JOE, HEX, VIC, TET, dTAMRA, TAMRA, NED, dROX, PET, BHQ, Gold540, or LIZ. Alternatively, the conditions may comprise DNA sequencing wherein the cohort further comprises two or more individuals with a mutation in SEQ ID NO: 1. The first reagent may be affixed to a substrate. The sample may be any sample including a sample comprising serum or a sample comprising one or more cells such as a pancreas biopsy or metastatic tumor sample. The method may also include collecting the sample from the subject. Classifying the subject into a group may be performed on the recommendation of a writing. The writing may be affixed to a container holding the tyrosine kinase inhibitor. The result may be any result including a ΔCt value, nucleic acid sequence data, or a photograph of stained tissue. The BTK inhibitor may be any BTK inhibitor including PCI-32765.

It is an object of the invention to provide a method for identifying a modulator of BTK. The method comprises (a) contacting a cancer cell overexpressing BTK with the modulator, wherein the cancer cell comprises inactivated DPC4 gene or gene product thereof; and (b) testing one or more cancer cell responses to the modulator, wherein the cancer cell response is chosen from cancer cell count, expansion, migration, metastasis, apoptosis; wherein the cancer cell response is compared relative to a control.

It is an object of the invention to provide a method of treating cancer patients, comprising administering to a patient a therapeutically effective amount of a pharmaceutical composition comprising PCI-32765.

It is an object of the invention to provide a kit comprising a pharmaceutical composition comprising PCI-32765 or its derivatives for treating cancer.

Other aspects and iterations of the invention are described in more detail below.

BRIEF DESCRIPTION OF THE FIGURES

A more complete understanding of the present invention may be derived by referring to the detailed description when considered in connection with the following illustrative figures.

Elements and acts in the figures are illustrated for simplicity and have not necessarily been rendered according to any particular sequence or embodiment.

(FIG. 2A) BxPC-3 based DPC4 isogenic cell lines, with and without DPC4 deficiency, respectively; (FIG. 2B) two different pancreatic cancer cell lines, BxPC-3 and PANC-1, with and without DPC4 deficiency, respectively; and (FIG. 2C) DPC4 isogenic colon cancer cell lines, HCT-116 (DPC4 wildtype) and HCT-116-DPC4-knockout.

(FIG. 3B) a pair of DPC4 isogenic colon cancer cell lines, HCT-116 and HCT-116-DPC4-knockout. The selectivity against the deficiency of DPC4 is significant in all candidate targets.

(FIG. 5B) that the dose dependent selective activity of PCI-32765 was consistent in the isogenic DPC4/SMAD4 colon cancer cell lines, HCT116 and HCT116 DPC4(-).

DETAILED DESCRIPTION OF THE INVENTION

Figure 1:
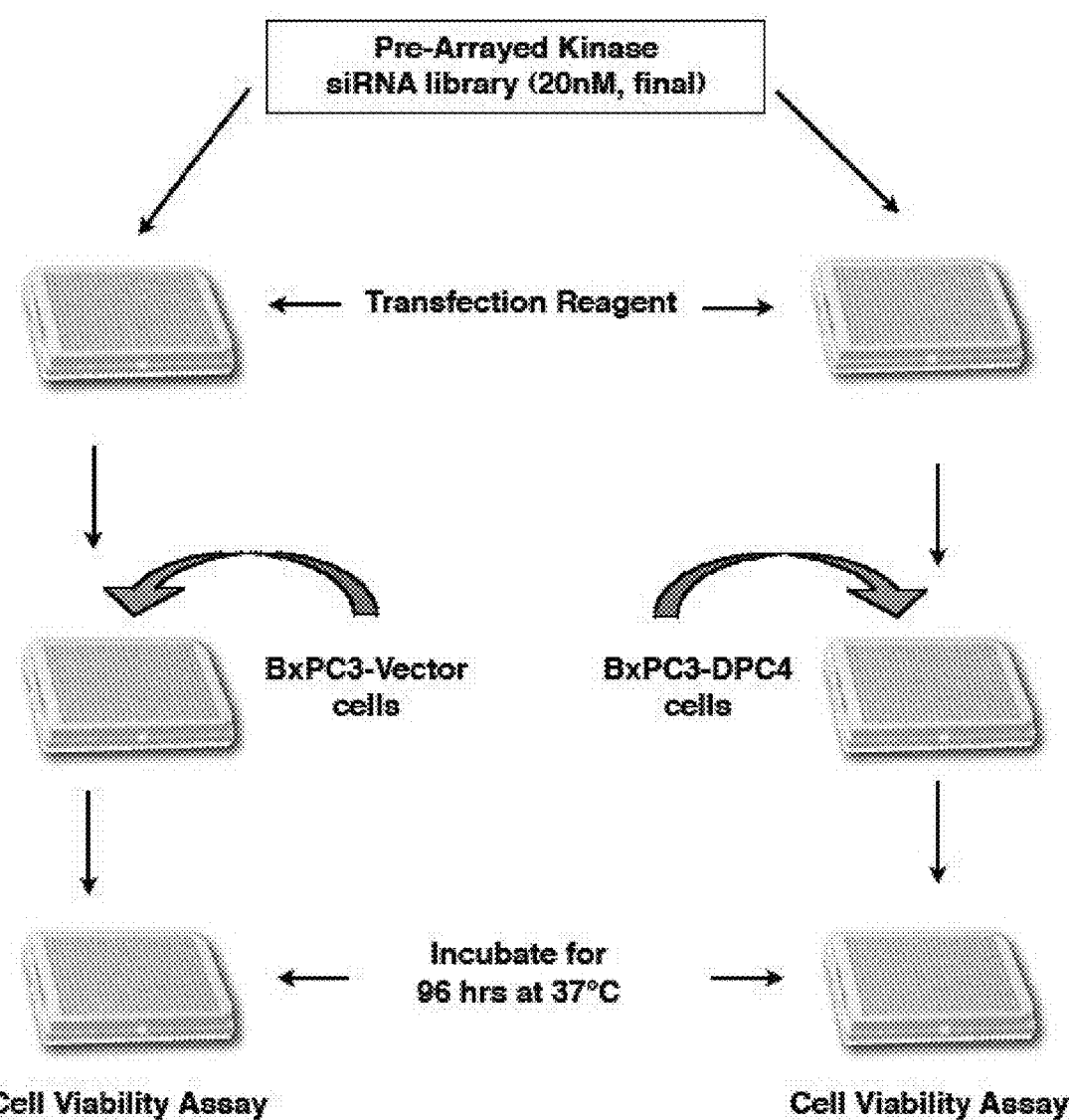
FIG. 1 depicts the workflow of the target screening using a kinase focused siRNA library and a DPC4 isogenic pair of pancreatic cell lines, BxPC3-Vector and BxPC3-DPC4 for selecting targets specific to cancer cells harboring mutations in the DPC4 gene.

Aspects and applications of the invention presented here are described in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶ 6. Thus, the use of the words "function," "means" or "step" in the Detailed Description or Description of the Drawings or claims is not intended to somehow indicate a desire to invoke the special provisions of 35 U.S.C. § 112, ¶ 6, to define the invention.

To the contrary, if the provisions of 35 U.S.C. § 112, ¶ 6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . "or "step for performing the function of . . . ," if the claims also recite any structure, material or acts in support of that means or step, or that perform the recited function, then it is the clear intention of the inventors not to invoke the provisions of 35 U.S.C. § 112, ¶ 6.

Moreover, even if the provisions of 35 U.S.C. § 112, ¶ 6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived or any other chemical structure. Examples of such nucleic acids include miRNA, tRNA, siRNA, mRNA, cDNA, or genomic DNA sequences including complimentary sequences. Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

Examples of molecules encompassed by a marker represented by a particular sequence or structure include alleles such as point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. The following nonlimiting examples are included for the purposes of clarifying this concept: If expression of a specific marker in a sample is assessed by RTPCR, and if the sample expresses an mRNA sequence different from the sequence used to identify the specific marker by one or more nucleotides, but the marker may still be detected using RTPCR, then the specific marker encompasses the sequence present in the sample. Alternatively if expression of a specific marker in a sample is assessed by an antibody and the amino acid sequence of the marker in the sample differs from a sequence used to identify marker by one or more amino acids, but the antibody is still able to bind to the version of the marker in the sample, then the specific marker encompasses the sequence present in the sample.

The concept of a marker also includes alleles in that the presence of an allele or other genetic variant in a cell or tumor cell are capable of signifying a mutated, inactive, silenced, truncated or otherwise non-functional biological molecule. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. The presence or absence of an allele may be detected through the use of any process through which a specific nucleic acid molecule may be detected, including direct and indirect methods of detecting the presence or absence of an allele. An allele may occur in a non-coding or coding region of a genome. If it is in a coding region, it may affect a particular triplet codon. If the allele does affect the codon, it may change the amino acid in the protein resulting from expression of the allele. The exception is if the allele is a silent mutation. In that case, the allele is a mutation in the coding region that does not change the amino acid that the codon encodes. An allele may also be called a mutation or a mutant. An allele may be compared to another allele that may be termed a wild type form of an allele. In some cases, the wild type allele is more common than the mutant.

Direct methods of detecting the presence of an allele include but are not limited to any form of DNA sequencing including Sanger, next generation sequencing, pyrosequencing, SOLID sequencing, massively parallel sequencing, pooled, and barcoded DNA sequencing or any other sequencing method now known or yet to be disclosed; PCR-based methods such as real-time PCR, quantitative PCR, quantitative real time PCR; allele specific ligation; comparative genomic hybridization; or any other method that allows the detection of a particular nucleic acid sequence within a sample or enables the differentiation of one nucleic acid from another nucleic acid that differs from the first nucleic acid by one or more nucleotides or any combination of these. Nucleic acids may include but need not be limited to RNA, cDNA, tRNA, mitochondrial DNA, plasmid DNA, siRNA, genomic DNA, or any other naturally occurring or artificial nucleic acid molecule. A subject may be any organism that may be infected by a bacterium including plants, animals, chordates, mammals, humans, insects, endangered species, or any other organism of agricultural, environmental, or other significance.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfyrlase enayme converts pyrophosphate into ATP which in turn catalyzes the conversion of luciferin to oxyluciferin which results in the generation of visible light that is then detected by a camera.

In SOLID sequencing, the molecule to be sequenced is fragmented and used to prepare a population of clonal magnetic beads (in which each bead is conjugated to a plurality of copies of a single fragment) with an adaptor sequence and alternatively a barcode sequence The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting an allele. Nucleic acid sequences may be identified by the IUAPC letter code which is as follows: A—Adenine base; C—Cytosine base; G—guanine base; T or U—thymine or uracil base. M—A or C; R—A or G; W—A or T; S—C or G; Y—C or T; K—G or T; V—A or C or G; H—A or C or T; D—A or G or T; B—C or G or T; N or X—A or C or G or T. Note that T or U may be used interchangeably depending on whether the nucleic acid is DNA or RNA. A sequence having less than 60% 70%, 80%, 90%, 95%, 99% or 100% identity to the identifying sequence may still be encompassed by the invention if it is able of binding to its complimentary sequence and/or facilitating nucleic acid amplification of a desired target sequence. If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence.

A nucleic acid may be added to a sample by any of a number of methods including manual methods, mechanical methods, or any combination thereof. The presence of the allele may be signified by any of a number of methods including amplification of a specific nucleic acid sequence, sequencing of a native or amplified nucleic acid, or the detection of a label either bound to or released from the nucleic acid. Addition of the nucleic acid to the sample also encompasses addition of the nucleic acid to a sample in which the target allele to which the nucleic acid has specificity is absent.

In some aspects of the invention, the presence of an allele may be established by binding to a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample and consequently the presence of the allele in the sample.

In allele-specific hybridization, oligonucleotide sequences representing all possible variations at a polymorphic site are included on a chip. The chip and sample are subject to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

Expression encompasses any and all processes through which material derived from a nucleic acid template may be produced. Expression thus includes processes such as RNA transcription, mRNA splicing, protein translation, protein folding, post-translational modification, membrane transport, associations with other molecules, addition of carbohydrate moeties to proteins, phosphorylation, protein complex formation and any other process along a continuum that results in biological material derived from genetic material whether in vitro, in vivo, or ex vivo. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, direct sequencing of genomic DNA, or any other method of detecting a specific nucleic acid now known or yet to be disclosed. Other examples include any process of assessing protein expression including flow cytometry, immunohistochemistry, ELISA, Western blot, and immunoaffinity chromatograpy, HPLC, mass spectrometry, protein microarray analysis, PAGE analysis, isoelectric focusing, 2-D gel electrophoresis, or any enzymatic assay or any method that uses a protein reagent, nucleic acid reagent, or other reagent capable of specifically binding to or otherwise recognizing a specific nucleic acid or protein marker.

Other methods used to assess expression include the use of such natural or artificial ligands capable of specifically binding a marker. Such ligands include antibodies, antibody complexes, conjugates, natural ligands, small molecules, nanoparticles, or any other molecular entity capable of specific binding to a marker. Antibodies may be monoclonal, polyclonal, or any antibody fragment including an Fab, F(ab)2, Fv, scFv, phage display antibody, peptibody, multi-specific ligand, or any other reagent with specific binding to a marker. Ligands may be associated with a label such as a radioactive isotope or chelate thereof, dye (fluorescent or nonfluorescent,) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Differential expression encompasses any detectable difference between the expression of a marker in one sample relative to the expression of the marker in another sample. Differential expression may be assessed by a detector, an instrument containing a detector, or by aided or unaided human eye. Examples include but are not limited to differential staining of cells in an IHC assay configured to detect a marker, differential detection of bound RNA on a microarray to which a sequence capable of binding to the marker is bound, differential results in measuring RTPCR measured in ⊗ Ct or alternatively in the number of PCR cycles necessary to reach a particular optical density at a wavelength at which a double stranded DNA binding dye (e.g. SYBR Green) incorporates, differential results in measuring label from a reporter probe used in a real-time RTPCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

The expression of the marker in a sample may be compared to a level of expression predetermined to predict the presence or absence of a particular physiological characteristic. The level of expression may be derived from a single control or a set of controls. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources. Comparison of the expression of the marker in the sample to a particular level of expression results in a prediction that the sample exhibits or does not exhibit the cellular or physiological characteristic.

Prediction of a cellular or physiological characteristic includes the prediction of any cellular or physiological state that may be predicted by assessing the expression of a marker. Examples include the identity of a cell as a particular cell including a particular normal or cancer cell type, the likelihood that one or more diseases is present or absent, the likelihood that a present disease will progress, remain unchanged, or regress, the likelihood that a disease will respond or not respond to a particular therapy, or any other disease outcome. Further examples include the likelihood that a cell will move, senesce, apoptose, differentiate, metastasize, or change from any state to any other state or maintain its current state.

Expression of a marker in a sample may be more or less than that of a level predetermined to predict the presence or absence of a cellular or physiological characteristic. The expression of the marker in the sample may be more than 1,000,000×, 100,000×, 10,000×, 1000×, 100×, 10×, 5×, 2×, 1×, 0.5×, 0.1×0.01×, 0.001×, 0.0001×, 0.00001×, 0.000001×, 0.0000001× or less than that of a level predetermined to predict the presence or absence of a cellular or physiological characteristic.

The invention contemplates assessing the expression of the marker in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. Samples include single cells, whole organs or any fraction of a whole organ, in any condition including in vitro, ex vivo, in vivo, post-mortem, fresh, fixed, or frozen.

One type of cellular or physiological characteristic is the risk that a particular disease outcome will occur. Assessing this risk includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Determining the level of expression or the presence of an allele that signifies a physiological or cellular characteristic may be assessed by any of a number of methods. The skilled artisan will understand that numerous methods may be used to select a level of expression for a particular marker or a plurality of markers that signifies a particular physiological or cellular characteristics. In diagnosing the presence of a disease, a threshold value may be obtained by performing the assay method on samples obtained from a population of patients having a certain type of disease (cancer for example,) and from a second population of subjects that do not have the disease. In assessing disease outcome or the effect of treatment, a population of patients, all of which have, a disease such as cancer, may be followed for a period of time. After the period of time expires, the population may be divided into two or more groups. For example, the population may be divided into a first group of patients whose disease progresses to a particular endpoint and a second group of patients whose disease does not progress to the particular endpoint. Examples of endpoints include disease recurrence, death, metastasis or other states to which disease may progress. If expression of the marker in a sample is more similar to the predetermined expression of the marker in one group relative to the other group, the sample may be assigned a risk of having the same outcome as the patient group to which it is more similar.

In addition, one or more levels of expression of the marker may be selected that provide an acceptable ability of its ability to signify a particular physiological or cellular characteristic. Examples of such characteristics include identifying or diagnosing a particular disease, assessing a risk of outcome or a prognostic risk, or assessing the risk that a particular treatment will or will not be effective.

For example, Receiver Operating Characteristic curves, or "ROC" curves, may be calculated by plotting the value of a variable versus its relative frequency in two populations. For any particular marker, a distribution of marker expression levels for subjects with and without a disease may overlap. This indicates that the test does not absolutely distinguish between the two populations with complete accuracy. The area of overlap indicates where the test cannot distinguish the two groups. A threshold is selected. Expression of the marker in the sample above the threshold indicates the sample is similar to one group and expression of the marker below the threshold indicates the sample is similar to the other group. The area under the ROC curve is a measure of the probability that the expression correctly indicated the similarity of the sample to the proper group. See, e.g., Hanley et al., *Radiology* 143: 29-36 (1982) hereby incorporated by reference.

Additionally, levels of expression may be established by assessing the expression of a marker in a sample from one patient, assessing the expression of additional samples from the same patient obtained later in time, and comparing the expression of the marker from the later samples with the initial sample or samples. This method may be used in the case of markers that indicate, for example, progression or worsening of disease or lack of efficacy of a treatment regimen or remission of a disease or efficacy of a treatment regimen.

Other methods may be used to assess how accurately the expression of a marker signifies a particular physiological or cellular characteristic. Such methods include a positive likelihood ratio, negative likelihood ratio, odds ratio, and/or hazard ratio. In the case of a likelihood ratio, the likelihood that the expression of the marker would be found in a sample with a particular cellular or physiological characteristic is compared with the likelihood that the expression of the marker would be found in a sample lacking the particular cellular or physiological characteristic.

An odds ratio measures effect size and describes the amount of association or non-independence between two groups. An odds ratio is the ratio of the odds of a marker being expressed in one set of samples versus the odds of the marker being expressed in the other set of samples. An odds ratio of 1 indicates that the event or condition is equally likely to occur in both groups. An odds ratio grater or less than 1 indicates that expression of the marker is more likely to occur in one group or the other depending on how the odds ratio calculation was set up. A hazard ratio may be calculated by estimate of relative risk. Relative risk is the chance that a particular event will take place. It is a ratio of the probability that an event such as development or progression of a disease will occur in samples that exceed a threshold level of expression of a marker over the probability that the event will occur in samples that do not exceed a threshold level of expression of a marker. Alternatively, a hazard ratio may be calculated by the limit of the number of events per unit time divided by the number at risk as the time interval decreases. In the case of a hazard ratio, a value of 1 indicates that the relative risk is equal in both the first and second groups; a value greater or less than 1 indicates that the risk is greater in one group or another, depending on the inputs into the calculation.

Additionally, multiple threshold levels of expression may be determined. This can be the case in so-called "tertile," "quartile," or "quintile" analyses. In these methods, multiple groups can be considered together as a single population, and are divided into 3 or more bins having equal numbers of individuals. The boundary between two of these "bins" may be considered threshold levels of expression indicating a particular level of risk of a disease developing or signifying a physiological or cellular state. A risk may be assigned based on which "bin" a test subject falls into.

A subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer. Methods of identifying subjects suspected of having cancer include but are not limited to: physical examination, family medical history, subject medical history, endometrial biopsy, or a number of imaging technologies such as ultrasonography, computed tomography, magnetic resonance imaging, magnetic resonance spectroscopy, or positron emission tomography.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The present invention further provides kits to be used in assessing the expression of a RNA in a subject to assess the risk of developing disease. Kits include any combination of components that facilitates the performance of an assay. A kit that facilitates assessing the expression of a RNA may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A specific nucleic acid may include a label. A label may be any substance capable of aiding a machine, detector, sensor, device, or enhanced or unenhanced human eye from differentiating a sample that that displays positive expression from a sample that displays reduced expression. Examples of labels include but are not limited to: a radioactive isotope or chelate thereof, a dye (fluorescent or nonfluorescent,) stain, enzyme, or nonradioactive metal. Specific examples include but are not limited to: fluorescein, biotin, digoxigenin, alkaline phosphatase, biotin, streptavidin, 3H, 14C, 32P, 35S, or any other compound capable of emitting radiation, rhodamine, 4-(4'-dimethylaminophenylazo) benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, and LIZ.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence.

In some aspects of the invention, the probe may be affixed to a solid substrate. In other aspects of the invention, the sample may be affixed to a solid substrate. A probe or sample may be covalently bound to the substrate or it may be bound by some non-covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate as (for example) the case of a Southern Blot, Northern blot or other method that affixes the sample to a substrate.

Kits may also contain reagents that detect proteins, often through the use of an antibody. These kits will contain one or more specific antibodies, buffers, and other reagents configured to detect binding of the antibody to the specific epitope. One or more of the antibodies may be labeled with a fluorescent, enzymatic, magnetic, metallic, chemical, or other label that signifies and/or locates the presence of specifically bound antibody. The kit may also contain one or more secondary antibodies that specifically recognize epitopes on other antibodies. These secondary antibodies may also be labeled. The concept of a secondary antibody also encompasses non-antibody ligands that specifically bind an epitope or label of another antibody. For example, streptavidin or avidin may bind to biotin conjugated to another antibody. Such a kit may also contain enzymatic substrates that change color or some other property in the presence of an enzyme that is conjugated to one or more antibodies included in the kit.

A kit may also contain an indication of a level of expression that signifies a particular physiological or cellular characteristic. An indication includes any guide to a level of expression that, using the kit in which the indication is provided, would signal the presence or absence of any physiological or cellular state that the kit is configured to detect. The indication may be expressed numerically, expressed as a color, expressed as an intensity of a band, derived from a standard curve, or derived from a control. The indication may be printed on a writing that may be included in the kit or it may be posted on the internet or embedded in a software package.

Where clinical applications are contemplated, it will be necessary to prepare pharmaceutical compositions that comprise expression vectors, virus stocks, proteins, antibodies or drugs in a form appropriate for the intended application. In many instances, this will entail preparing compositions that are essentially free of pyrogens, as well as other impurities that could be harmful to humans or animals. A pharmaceutical composition includes an active component such as Temozolomide, an inhibitor of a marker or other compound and a pharmacologically acceptable carrier. Pharmaceutically acceptable carriers include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic or prophylactic compositions is contemplated. Supplementary active ingredients also can be incorporated into the compositions.

Pharmaceutical compositions include classic pharmaceutical preparations. Administration of these compositions according to the present invention will be via any common route so long as the marker tissue is available via that route. This includes oral, nasal, buccal, rectal, vaginal or topical. Alternatively, administration may be by orthotopic, intradermal, subcutaneous, intramuscular, intraperitoneal intratumoral, circumferentially, catheterization, or intravenous injection. Such compositions would normally be administered as pharmaceutically acceptable compositions. In some aspects of the invention, the pharmaceutical composition is formulated in such a way that it is capable of crossing the blood-brain barrier. However, in other aspects of the invention, the pharmaceutical composition may be administered directly to a tumor or placed in close proximity to a tumor.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms. Expansion of a cancer cell includes any process that results in an increase in the number of individual cells derived from a cancer cell.

Expansion of a cancer cell may result from mitotic division, proliferation, or any other form of expansion of a cancer cell, whether in vitro or in vivo. Expansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include caspase dependent and independent pathways, autophagy, necrosis, apoptosis, and mitochondrial dependent and independent processes and further include any such processes yet to be disclosed.

In some aspects of the invention, inhibition of the expansion of the cancer cell is achieved through the use of an outside agent applied to the cancer cell for the purpose of slowing the expansion of the cancer cell. Such agents include natural or synthetic ligands, blockers, agonists, antagonists, or activators of receptors, immune cells such as CD8+ T cells, viruses, inhibitors of gene or protein expression such as siRNA or miR's, small molecules, pharmaceutical compositions, or any other composition of matter that when administered to the cancer cell would result in the slowing of the expansion of the cancer cell. The concept of agents that slow the expansion of a cancer cell encompasses restricting access to any natural or artificial agent necessary for cell survival including necessary nutrients, ligands, or cell-cell contacts. Examples of such agents and conditions include treatment with antiangiogenic inhibitors.

In some aspects of the invention, the agent that slows the expansion of the cancer cell comprises a Bruton's Tyrosine Kinase inhibitor. Generally, tyrosine kinases catalyze the transfer of a phosphate group to the tyrosine residue of a specific protein. If the tyrosine kinase inhibitor (TKI) inhibits the action of a kinase necessary for expansion, differentiation or division of a cancer cell, expansion of the cancer cell will be slowed. A TKI includes any agent that inhibits the action of one or more tyrosine kinases in a specific or non-specific fashion. TKI's may include small molecules, antibodies, peptides, or anything that directly, indirectly, allosterically, or in any other way inhibits tyrosine residue phosphorylation.

The present invention provides a therapeutic target for cancers associated with inactivation of DPC4 gene. Specifically, the inhibition of the target reduced cancer cell growth. In this regard, the present invention provides a method for screening inhibitor to therapeutic targets such as BTK.

One of the main genetic alterations in pancreatic cancer is the loss-of-function mutation of the deleted in pancreatic cancer locus 4 (DPC4) tumor-suppressor gene. The DPC4 gene is located on chromosome 18q21, a region that is homozygously deleted in 30% to 37% pancreatic ductal adenocarcinomas. Also, intragenic inactivating mutations, such as nonsense, misssense, and frameshift, occur commonly in the DPC4 gene. The DPC4 gene is inactivated in □55% of tumors taken directly form patients. The loss of DPC4 gene is thought to be associated with the progression and malignancy of pancreatic cancer, as it occurs only in PanIN3 (Pancreatic Intraepithelial Neoplasia) and pancreatic adenocarcinomas. DPC4 deficiency is also associated with poor survival of patients with pancreatic cancer. Patients with pancreatic cancer with normal DPC4 protein expression have a significantly longer survival. The loss of DPC4 is also associated with progression and malignancy in other types of tumor, such as colorectal tumors at varying stages, intramucosal carcinomas, in invasive carcinomas without distant metastases, in primary invasive carcinomas with distant metastases, and in carcinomas metastasized to the liver or distant lymph nodes.

In one embodiment of the present invention, siRNAs were used to screen targets that are critical to the viability of cancer cells with DPC4 deficiency. In other embodiment, target screening can be conducted using inhibitive agents that selectively kill cancer cells with one or more inactivated tumor-suppressor genes. The screen further uses a pair of cells with different genotype, mutated versus wildtype, in one or more specific tumor suppressor genes. The cell may be The human pancreatic adenocarcinoma cell lines such as BxPC-3, AsPC-1, Capan-1, Capan-2, CFPAC-1, Hs 766T, MIA PaCa-2, PANC-1, SU.86.86, or other suitable cell lines in the American Type Culture Collection (Rockville, Md.). In one embodiment, the cells are an isogenic pair with only difference in the specific tumor suppressor gene. In one exemplary example, the pair of isogenic cells are BxPC3-vector (having the homozygous deletion of DPC4 gene) and BxPC3-DPC4 (having the DCP4 gene restored in the BxPC-3-vector).

In on embodiment, BxPC3-Vector and BxPC3-DPC4 were treated by the siRNA library oligos in parallel and the effects of the siRNA oligos on the growth of the cell lines were then compared. In one embodiment, the siRNA library is kinase focused in that it consisted of two siRNA oligonucleotides for each of the 624 validated protein kinase genes. siRNA oligos that selectively inhibited the cell growth of BxPC3-Vector cell line were selected as potential positive gene hits. The genes so selected and validated represent potential therapeutic targets that are very specific to cancer cells harboring mutations in the DPC4 gene. One of the gene hits provided by this invention is the Bruton tyrosine kinase (BTK, UniProtKB/Swiss-Prot Accession No: Q06187). Other validated gene targets include FLCN, LARS2, PSMB8, SPR, and RAB7.

BTK is a member of the Tec family that is critically important for the growth, differentiation and activation of B-cells. More than 600 different mutations in the BTK gene have been found to cause X-linked agammaglobulinemia (XLA). XLA is one of the most frequent inherited immunodeficiency diseases in man and is characterized by an almost complete arrest of B cell differentiation at the pre-B cell stage. Most of the BTK mutations result in the absence of the BTK protein. Other mutations change a single protein building block (amino acid), which probably leads to the production of an abnormal BTK protein that is quickly broken down in the cell. The absence of functional BTK protein blocks B cell development and leads to a lack of antibodies, causing an increased susceptibility to infections in people with XLA.

BTK-mediated B cell receptor signaling appears to be required for the survival of immature B cells in the bone marrow, that have performed a successful immunoglobulin (Ig) L chain locus rearrangement, resulting in the expression of a non-autoreactive Ig on the membrane. BTK is also involved in signaling pathways that govern the development of peripheral B cells, including follicular entry, follicular maturation and plasma cell differentiation. Activated BTK is involved in the phosphorylation of a number of signaling molecules involved in the PLC-gamma, JNK (c-Jun N-terminal kinase) and p38 MAPK (mitogen-activated protein kinases) signal transduction pathways, leading to Ca2+ mobilization, mRNA stabilization and the induction of NF-kappaB and AP-1 transcription factors. BTK activity is negatively regulated by a number of proteins including inhibitor of BTK (IBTK), Sab (a JNK-interacting protein) and c-Cbl (the product of the protooncogene c-Cbl). Mutations in this enzyme are known in humans and result in the immunological disorder X-linked agammaglobulemia.

Folliculin (FLCN) gene is located within the Smith-Magenis syndrome region on chromosome 17. Mutations in this gene are associated with Birt-Hogg-Dube syndrome, which is characterized by fibrofolliculomas (an inherited disorder of the hair follicle), renal tumors, lung cysts, and pneumothorax. Alternative splicing of this gene results in two transcript variants encoding different isoforms. The protein product of this gene (UniProtKB/Swiss-Prot Accession No: Q8NFG4) may play a role in the pathogenesis of an uncommon form of kidney cancer through its association with fibrofolliculomas; it may also be a tumor suppressor involved in colorectal tumorigenesis; and it may be involved in energy and/or nutrient sensing through the AMPK and mTOR signaling pathways.

LARS2 (leucyl-tRNA synthetase 2, mitochondrial) encodes a class 1 aminoacyl-tRNA synthetase, mitochondrial leucyl-tRNA synthetase. (UniProtKB/Swiss-Prot Accession No: Q15031). Each of the twenty aminoacyl-tRNA synthetases catalyzes the aminoacylation of a specific tRNA or tRNA isoaccepting family with the cognate amino acid.

PSMB8 (proteasome subunit, beta type, 8) encodes a member of the proteasome B-type family, also known as the T1B family, that is a 20S core beta subunit (UniProtKB/Swiss-Prot Accession No: P28062). This gene is located in the class II region of the MHC (major histocompatibility complex). Expression of this gene is induced by gamma interferon and this gene product replaces catalytic subunit 3 (proteasome beta 5 subunit) in the immunoproteasome. Proteolytic processing is required to generate a mature subunit. Two alternative transcripts encoding two isoforms have been identified; both isoforms are processed to yield the same mature subunit.

SPR (sepiapterin reductase) encodes an aldo-keto reductase (UniProtKB/Swiss-Prot Accession No: P35270) that catalyzes the NADPH-dependent reduction of pteridine derivatives and is important in the biosynthesis of tetrahydrobiopterin (BH4). Mutations in this gene result in DOPA-responsive dystonia due to sepiaterin reductase deficiency.

RAB7 (RAB7A, member RAS oncogene family) encodes a RAB family member (UniProtKB/Swiss-Prot Accession No: P51149) that regulates vesicle traffic in the late endosomes and also from late endosomes to lysosomes. This encoded protein is also involved in the cellular vacuolation of the VacA cytotoxin of *Helicobacter pylori*. Mutations at highly conserved amino acid residues in this gene have caused some forms of Charcot-Marie-Tooth (CMT) type 2 neuropathies.

Among the various aspects of the present invention is the provision of a target for cancer treatment, specifically for cancers associated with inactivated DCP4 gene. Generally, a target may be any molecular structure produced by a cell, expressed inside the cell, accessible on the cell surface, or secreted by the cell, whose activity may be modified by a drug and the modification results in a desirable therapeutic effect. A target may be any protein, carbohydrate, fatty acids, nucleic acid, catalytic site, or any combination of these such as an enzyme, glycoprotein, ion channels, receptors, cell membrane, virus, cell, organ, organelle, or any uni- or multimolecular structure or any other such structure now known or yet to be disclosed whether alone or in combination.

Specifically in this invention, a target may be represented by a nucleic acid sequence, the protein or peptide or the fragments thereof encoded by the nucleic acid sequence. Examples of such nucleic acid sequence include miRNA, tRNA, siRNA, mRNA, cDNA, or genomic DNA sequences. In one embodiment, therefore, the term "target" encompasses a gene and a gene allele thereof, and the products (i.e., RNA and protein) of the gene or a gene allele thereof, whose expression or activity is directly or indirectly associated with a particular phenotype or cellular condition, or physiological characteristic.

An allele includes any form of a particular nucleic acid that may be recognized as a particular form on account of its location, sequence, chemical modification of the sequence, expression level, expression specificity or any other characteristic that may identify it as being a form of the particular gene. Variable alleles of a particular gene may differ from each other because of point mutations, silent mutations, deletions, insertions, frameshift mutations, single nucleotide polymorphisms (SNPs), inversions, translocations, heterochromatic insertions, differentially epigenetically modified, or any combination of thereof, relative to a reference gene. An allele may be compared to another allele that may be termed a wild type form of an allele. In comparison to the wild type allele, a different allele may be called a mutation or a mutant. Mutants may also be interchangeably called variants. In some cases, the wild type allele is more common than the mutant. In the example of gene mutation, the mutation may be in the coding region or the non-coding region. The non-coding region comprises transcriptional and translational control elements. Suitable transcription or translation control elements include but are not limited to upstream control elements, enhancer elements, TATA boxes, cis regulatory regions, activator binding regions, repressor binding regions, transcription initiation sites, polyadenylation control elements, transcription termination sites, ribosome binding sites, translation initiation sites, and translation termination sites.

An allele of a gene may have overexpression, underexpression or no expression. Alternatively, an allele of a gene may or may not produce a functional protein. A gene allele may produce a protein with altered sequence, function, localization, stability, dimerization, protein-protein interaction, or temporal or spacial expression specificity. A genetic mutation or variance may be any detectable change in genetic material such as DNA, or a corresponding change in the RNA or protein product of that genetic material.

At the protein level of a target, there may be conserved variants to a given amino acid residue of the protein, peptide or fragments thereof. In a conserved variant, the amino acid has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Depending on the location of the variance in the overall context of the protein, some substitution may have little or no effect on the apparent molecular weight or isoelectric point of the protein or polypeptide.

Amino acids other than those indicated as conserved may differ in a protein or peptide so that the percent protein or amino acid sequence identity between any two proteins of similar function may vary as determined according to an alignment scheme such as by the Cluster Method. The term "sequence identity" in the context of protein refers to the extent in which two amino acid sequences are invariant, i.e., the two sequences have the same amino acid at the same position. Sequence identity is generally expressed as a percentage. Two amino acid sequences that are identical in sequence and length have 100% sequence identity. The concept of a variant encompasses a polypeptide or the fragment thereof which has at least 60%, 75%, 85%, 90%, or 95% amino acid identity as determined by algorithms such as BLAST or FASTA and which has the same or substantially similar properties and/or activities as the native or parent protein or enzyme to which it is compared.

Another example of allele or variant is a gain-of-function variant. Gain-of-function variants of a polypeptide encompass any variant in which a change in one or more amino acid residues in a polypeptide improves the activity of the polypeptide. Examples of activities of a polypeptide that may be improved by a change resulting in a gain of function variant include but are not limited to enzymatic activity, binding affinity, phosphorylation or dephosphorylation efficiency, activation, deactivation, or any other activity or property of a protein that may be quantitatively measured by some method now known or yet to be disclosed.

In one embodiment of the invention, the target for cancer cells is chosen from BTK, FLCN, LARS2, PSMB8, SPR, and RAB7, which comprises the coding nucleic acid sequence and its alleles, the polypeptide products and variants thereof.

The presence or absence of an allele may be detected through the use of any process known in the art, including using primers and probes designed according to a specific allele for PCR, sequencing, hybridization, immunohistochemical analyses.

Disclosed herein are methods for identifying agents that alter the expression or activity of a therapeutic target resulting in a desirable therapeutic effect. Preferably, the target for a therapeutic agent is BTK. The methods include contacting a test agent with a cell comprising a therapeutic target having increased expression in comparison to a control cell, the target being BTK. In one exemplary example, an agent that has therapeutic effect may be identified by determining the effect of a test agent on the expression level of a target. In a particular example, a test agent that down-regulates the target expression as compared to the target expression in the absence of the test agent identifies that test agent as an inhibitor of a target; and specifically in the present invention, the target is for pancreatic cancer cell proliferation and migration and the agent is an inhibitor to the target and thus alleviate these properties of the pancreatic cancer cell.

Agents that interact with a therapeutic target to result in a desirable therapeutic effect may include a pharmaceutically active ingredient or pharmaceutically acceptable salt thereof, a drug, a toxin, a chemical, a small organic molecule, a large molecule or peptide or an antibody. Large-molecule pharmaceuticals refer to pharmaceutical agents having a molecular weight greater than about 1000 daltons, e.g. peptidic drugs, vaccines and hormones. The term "antibody" is used herein in the broadest sense and refers generally to a molecule that contains at least one antigen binding site that immunospecifically binds to a particular antigen target of interest. Antibody thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term thus includes full length antibodies and/or their variants as well as immunologically active fragments thereof, thus encompassing, antibody fragments capable of binding to a biological molecule (such as an antigen or receptor) or portions thereof, including but not limited to Fab, Fab', F(ab')2, facb, pFc', Fd, Fv or scFv (See, e.g., CURRENT PROTOCOLS IN IMMUNOLOGY, (Colligan et al., eds., John Wiley & Sons, Inc., NY, 1994-2001).

The screening or creation, identification and selection of appropriate therapeutic agent through the target identified herein can be accomplished by a variety of methods. One approach is to use structural knowledge about the target protein to design a candidate molecule with which it will precisely interact. An example would be computer assisted molecular design. A second approach is to use combinatorial or other libraries of molecules, whereby a large library of molecules is screened for inhibitory effect with regard to the target gene or protein expression, or ability to inhibit the transcriptional factor activity of the target protein. In a further example, a panel of antibodies may be screened for ability to inhibit the target protein.

Cancer and precancer may be thought of as diseases that involve unregulated cell growth. Metastasis involves migration of tumor cells away from the site of the primary tumor, entry into the circulation, and proliferation at a new site. Cell growth involves a number of different factors. One factor is how rapidly cells proliferate, and another involves how rapidly cells die. Cells can die either by necrosis or apoptosis depending on the type of environmental stimuli. Cell motility is yet another factor that influences tumor growth kinetics and metastasis. Resolving which of the many aspects of cell growth a test agent affects can be important to the discovery of a relevant pharmaceutical therapy for pancreatic cancer cells. Screening assays based on this technology can be combined with other tests to determine which agents have growth inhibiting and pro-apoptotic activity in pancreatic cancer cells.

Some embodiments provided herein involve determining the ability of a given agent to inhibit the increased expression of a target in cancer cells. In one preferred embodiment, the target is BTK. In one preferred embodiment, the cancer cell is associated with inactivated DPC4 gene. Various cell lines can be used, which may be selected based on the tissue to be tested. Certain cell lines are well characterized, and are used for instance by the United States National Cancer Institute (NCI) in their screening program for new anti-cancer drugs. Suitable pancreatic cancer cell lines include but not limited to A818.1, AsPc-1, BxPC-3, Capan-1, Capan-2, CF PAC-1, Colo 357, FA6, HPDE6, Hs766T, MIA PaCa-2, MDA Panc-3, PaCa-3, Panc-1, PaTuI, PaTuII, QGP-1, Rossi, RWP-1, Suit-2, Su8686, SW-979, T3M-4, and derivatives thereof. There are also suitable cancer cell or cell line cell for fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells for therapeutic agent screening include blood borne cancers such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

Cell lines can also be constructed to overexpress BTK for screening inhibitory agents for cancer cell growth, or specifically cancer cells with inactivated DPC4 gene. In addition to cell line cells, cells or samples originated from biopsy or other in vivo or ex vivo analysis of various cancer may be used. In some aspects of the invention, the sample may be a body fluid sample, such as peripheral blood, serum, plasma, lymph fluid, ascites, serous fluid, pleural effusion, sputum, cerebrospinal fluid, amniotic fluid, lacrimal fluid, gastric fluid, pancreatic fluid, mucus or urine, from which free floating DNA, RNA, protein, peptide or fragments thereof may be detected and compared to control samples. Samples include single cells, whole organs or any fraction of a whole organ, in any condition including in vitro, ex vivo, in vivo, post-mortem, fresh, fixed, or frozen. Alternatively, a sample may be any cell source from which DNA, including genomic, somatic, and germline DNA may be obtained.

Significant tumor cell growth inhibition, greater than about 30% at a dose of 100 μM or below, is further indicative that the agent is useful for treating neoplastic lesions. An $IC_{50}$ value may be determined and used for comparative purposes. This value is the concentration of drug needed to inhibit tumor cell growth by 50% relative to the control. In some embodiments, the $IC_{50}$ value is less than 100 μM in order for the agent to be considered further for potential use for treating, ameliorating, or preventing neoplastic lesions or tumor metastasis.

In another embodiment, test agents can be screened for induction of apoptosis, or cell death, using cultures of pancreatic tumor cells comprising BTK as a target. In some examples of such screening methods, treatment of cells with test agents involves either pre- or post-confluent cultures and treatment for one to seven days at various concentrations of the test agents. Apoptotic cells can be measured in both the attached and "floating" portions of the cultures. Both are collected by removing the supernatant, trypsinizing the attached cells, and combining both preparations following a centrifugation wash step (for example, 10 minutes, 2000 rpm). Following treatment with a test agent, cultures can be assayed for apoptosis and necrosis, for instance by florescent microscopy following labeling with acridine orange and ethidium bromide. Many methods for measuring apoptotic cells are known to those of ordinary skill in the art; for instance, one method for measuring apoptotic cell number has been described by Duke & Cohen (Curr. Prot. Immuno., Coligan et al., eds., 3.17.1-3.17.1, 1992). For example, floating and attached cells are collected by trypsinization and washed three times in PBS. Aliquots of cells are then centrifuged. The pellet is resuspended in media and a dye mixture containing acridine orange and ethidium bromide prepared in PBS and mixed gently. The mixture then can be placed on a microscope slide and examined for morphological features of apoptosis.

Apoptosis also can be quantified by measuring an increase in DNA fragmentation in cells that have been treated with test agents. Commercial photometric enzyme immunoassays (EIA) for the quantitative in vitro determination of cytoplasmic histone-associated-DNA-fragments (mono- and oligo-nucleosomes) are available (e.g., Cell Death Detection ELISA, Boehringer Mannheim). The Boehringer Mannheim assay is based on a sandwich-enzyme-immunoassay principle, using mouse monoclonal antibodies directed against DNA and histones, respectively. This allows the specific determination of mono- and oligo-nucleosomes in the cytoplasmic fraction of cell lysates. According to the vendor, apoptosis is measured as follows: The sample (cell-lysate) is placed into a streptavidin-coated microtiter plate ("MTP"). Subsequently, a mixture of anti-histone-biotin and anti-DNA peroxidase conjugates is added and incubated for, for example, about two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

Statistically significant increases of apoptosis (i.e., greater than 2 fold stimulation at a test agent concentration of 100 μM) are further indicative that the agent is useful for treating neoplastic lesions. Preferably, the $EC_{50}$ value for apoptotic activity should be less than 100 μM for the agent to be further considered for potential use for treating neoplastic lesions. $EC_{50}$ is understood herein to be the concentration that causes 50% induction of apoptosis relative to vehicle treatment.

In another embodiment, agents can be screened for inhibitory effects to the activity of BTK as a regulator of its substrate, which may be a protein or the gene encoding the protein substrate. In one preferred embodiment, the screening of inhibitory agents is achieved through determine the expression or activity of genes, known to be specifically regulated by BTK.

The method of determine the expression of a gene or the activity of its gene product, whether for the target itself or the substrate of the target, include but not limited to microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing. Other examples include any method of assessing biomarker protein expression such as flow cytometry, immunohistochemistry, ELISA, Western blot, and immunoaffinity chromatography, HPLC, mass spectrometry, protein microarray analysis, PAGE analysis, isoelectric focusing, 2-D gel electrophoresis, or any enzymatic assay.

Other methods used to assess a gene or protein expression include the use of natural or artificial ligands capable of specifically binding the protein. Such ligands include antibodies (as defined in paragraph 0027), antibody complexes, conjugates, natural ligands, small molecules, nanoparticles, or any other molecular entity capable of specific binding to a target. Ligands may be associated with a label such as a radioactive isotope or chelate thereof, dye (fluorescent or nonfluorescent,) stain, enzyme, metal, or any other substance capable of aiding a machine or a human eye from differentiating a cell expressing a target/substrate from a cell not expressing such.

Differential expression may be assessed by a detector, an instrument containing a detector, or by aided or unaided human eye. Examples include but are not limited to differential staining of cells in an IHC assay configured to detect a target, differential detection of bound RNA on a microarray to which a sequence capable of binding to the target is bound, differential results in measuring RT-PCR measured in ΔCt or alternatively in the number of PCR cycles necessary to reach a particular optical density at a wavelength at which a double stranded DNA binding dye (e.g. SYBR Green) incorporates, differential results in measuring label from a reporter probe used in a real-time RT-PCR reaction, differential detection of fluorescence on cells using a flow cytometer, differential intensities of bands in a Northern blot, differential intensities of bands in an RNAse protection assay, differential cell death measured by apoptotic markers, differential cell death measured by shrinkage of a tumor, or any method that allows a detection of a difference in signal between one sample or set of samples and another sample or set of samples.

Techniques using microarrays may also be advantageously implemented to detect assess gene expression. Gene expression may be that of the target or the expression of another set of genes upstream or downstream in a pathway of which the target is a component or a regulator. In one embodiment, microarrays may be designed so that the same set of identical oligonucleotides is attached to at least two selected discrete regions of the array, so that one can easily compare a normal sample, contacted with one of said selected regions of the array, against a test sample, contacted with another of said selected regions. Examples of microarray techniques include those developed by Nanogen, Inc. (San Diego, Calif.) and those developed by Affymetrix (Santa Clara, Calif.). However, all types of microarrays, also called "gene chips" or "DNA chips", may be adapted for the identification of mutations. Such microarrays are well known in the art.

PCI-32765 is a selective and irreversible BTK inhibitor that is currently in Phase I clinical trials in patients with B cell malignancies. As a BTK inhibitor, PCI-32765 blocks BCR (B cell receptor) signaling in human B cells but does not affect T cell receptor (TCR) signaling. BTK also functions in FcR1 signaling in mast cells, and PCI-32765 is a potent inhibitor of mast cell and basophil degranulation. In mice, orally dosed PCI-32765 reduced the level of circulating autoantibodies and reversed the course of collagen induced arthritis. PCI-32765 also inhibited auto-antibody production and the development of kidney disease in the MRL/lpr lupus model. Finally, PCI-32765 induced objective clinical responses in dogs with spontaneous B cell non-Hodgkin lymphoma. Therefore, PCI-32765 is a therapeutic approach for treating many different human diseases associated with activation of B cells. Additionally, other BTK inhibitors may be used, such as those described in U.S. Published Patent Application Nos. 20100324050, 20100331350, 20110039868, 20110008257, 20110086866, the contents of which are incorporated herein by reference.

PCI-45292 is a lead compound showing >2500-fold selectivity for BTK inhibition over other tyrosine kinases including EGFR and JAK-3. PCI-45292 is more potent in a mouse model of collagen-induced arthritis than BTK inhibitor PCI-32765. The estimated ED50 for once daily oral administration of PCI-45292 in the mouse model was 0.5 to 0.6 mg/kg/day. Based on interspecies scaling, human efficacious doses of PCI-45292 are predicted to be 10 mg or less. PCI-45292 as a BTK inhibitor will delay disease progression in rheumatoid arthritis patients and thus is classified as disease modifying anti-rheumatic drugs.

Therefore, another aspect of the invention, based on the new indication of PCI-32765, provides for pharmaceutical compositions comprising PCI-32765, the derivatives thereof or any combination of the above. The derivatives of PCI-32765 may be known or yet to be discovered. In general, the pharmaceutical composition will comprise an effective dosage amount of PCI-32765, i.e., an amount of PCI-32765 sufficient to provide treatment to the subject being administered the pharmaceutical composition. The amount of PCI-32765 in such pharmaceutical compositions, therefore, may range from about 97%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or about 3% by weight of the total amount of the various forms of PCI-32765.

A variety of excipients commonly used in pharmaceutical formulations may be selected on the basis of several criteria such as, e.g., the desired dosage form and the release profile properties of the dosage form. Non-limiting examples of suitable excipients include an agent selected from the group consisting of a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinilpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may be a non-effervescent disintegrant. Suitable examples of non-effervescent disintegrants include starches (such as corn starch, potato starch, and the like), pregelatinized and modified starches thereof, sweeteners, clays (such as bentonite), microcrystalline cellulose, alginates, sodium starch glycolate, and gums (such as agar, guar, locust bean, karaya, pecitin, and tragacanth).

In another embodiment, the excipient may be an effervescent disintegrant. By way of non-limiting example, suitable effervescent disintegrants include sodium bicarbonate in combination with citric acid, and sodium bicarbonate in combination with tartaric acid.

The excipient may comprise a preservative. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be utilized.

In another embodiment, the excipient may include a diluent. Diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

The excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot).

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *stevia*-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose.

Depending upon the embodiment, it may be desirable to provide a coloring agent. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

In various embodiments, the excipient may include a pH modifier. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein may be manufactured in one or several dosage forms. Suitable dosage forms include transdermal systems or patches. The transdermal system may be a matrix system, a reservoir system, or a system without rate-controlling membranes. Other suitable dosage forms also include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration; suspensions; emulsions; semisolids; or gels.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

The amount of active ingredient that is administered to a subject can and will vary depending upon a variety of factors such as the age and overall health of the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

The invention further provides kits comprising a pharmaceutical composition comprising PCI-32765 and/or its derivatives for treating cancers, particularly for cancers associated with inactivated DPC4 gene. The kit may further comprise a complete regimen of components that facilitate the administration of the pharmaceutical compositions. An example of such a kit includes one or more units of effective amounts or dosages of the compositions. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the kit comprises the container that encloses the unit dosage. The kit may further comprise instructions for the safe and effective use of the pharmaceutical composition for treating cancers.

EXAMPLES

Elements and acts in the examples are intended to illustrate the invention for the sake of simplicity and have not

Example 1

The Deleted in Pancreatic Cancer locus 4 (DPC4) is a tumor suppressor gene that is often inactivated in pancreatic and colorectal cancers. In pancreatic adenocarcinomas, the frequency of inactivation of DPC4 is approximately 55%, while in colorectal carcinomas has been reported to be 10% to 35%. The loss of DPC4 has been shown to be associated with the progression and malignancy of pancreatic cancer along with decreased patient survival. A small interfering (siRNA) library based screening strategy was employed to identify potential synthetic lethal partners of the DPC4 gene. A kinase focused siRNA library that consisted of two siRNA oligonucleotides for each of the 624 protein kinase genes was used. A DPC4 isogenic pair, (BxPC3 Vector and BxPC3-DPC4) (Wang et al. 2006) was treated with siRNA oligonucleotides in parallel and the effects of the siRNA oligonucleotides on the growth of the cell lines were then compared. SiRNA oligonucleotides that selectively inhibited expansion of the BxPC3-Vector cell line were selected as potential positive hits. These genes, once validated, represented potential drug targets that are very specific to cancer cells harboring mutations in the DPC4 gene. One of the top-ranked hits from this screening was Bruton agammaglobulinemia tyrosine kinase (BTK). With BTK siRNA treatment, BxPC3-Vector cells, which are DPC4 null, showed ~30% greater cell growth inhibition than the BxPC3-DPC4 cells, which express DPC4. This selectivity of BTK siRNA against DPC4 null cells was further confirmed in a screen using two pancreatic cancer cell lines, BxPC3 and PANC-1, which are DPC4 null and DPC4 expressing, respectively. BTK siRNA also showed significant selectivity against DPC4 deficiency in another pair of DPC4 isogenic colon cancer cell lines, HCT-116 and HCT-116-DPC4-knockout. To validate the BTK siRNA selectivity findings, we evaluated the BTK inhibitor PCI-32765 in our cancer cell line models and observed the same selectively against DPC4 null pancreatic and colon cancer cell lines. These results indicate that BTK is a potential molecular target for pancreas, colon, and other cancers harboring inactivating mutations in the DPC4 gene.

Figure 2A:
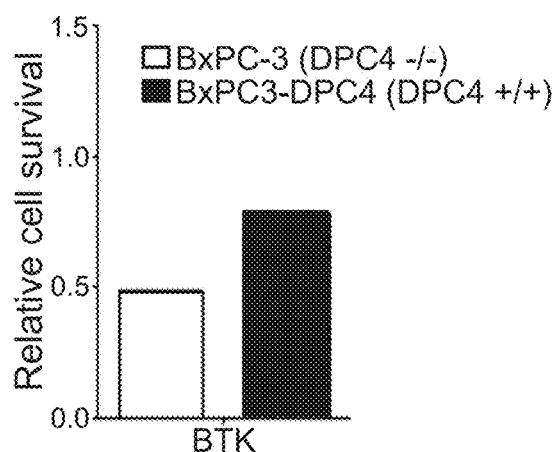
FIGS. 2A-2C depict that siRNA oligonucleotides targeting BTK gene selectively inhibit the growth of DPC4 null cancer cells were observed in three cell line models.
Figure 2B:
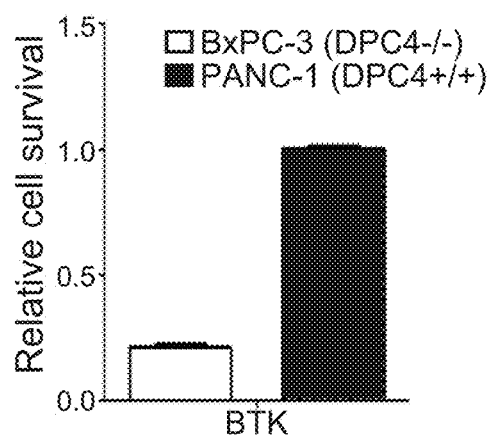
Figure 3A:
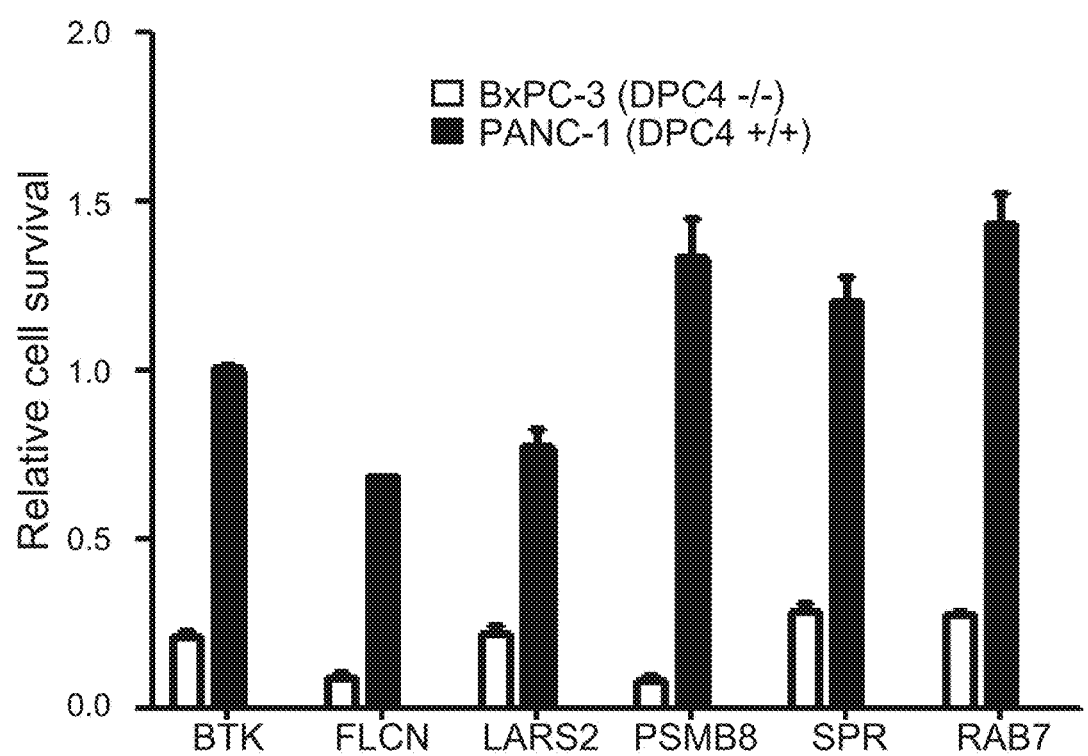
FIGS. 3A and 3B depict confirmation screen of BTK, FLCN, LARS2, PSMB8, SPR, and RAB7 using (FIG. 3A) two pancreatic cancer cell lines, BxPC3 and PANC-1, which are DPC4 null and DPC4 wildtype, respectively.
Figure 3B:
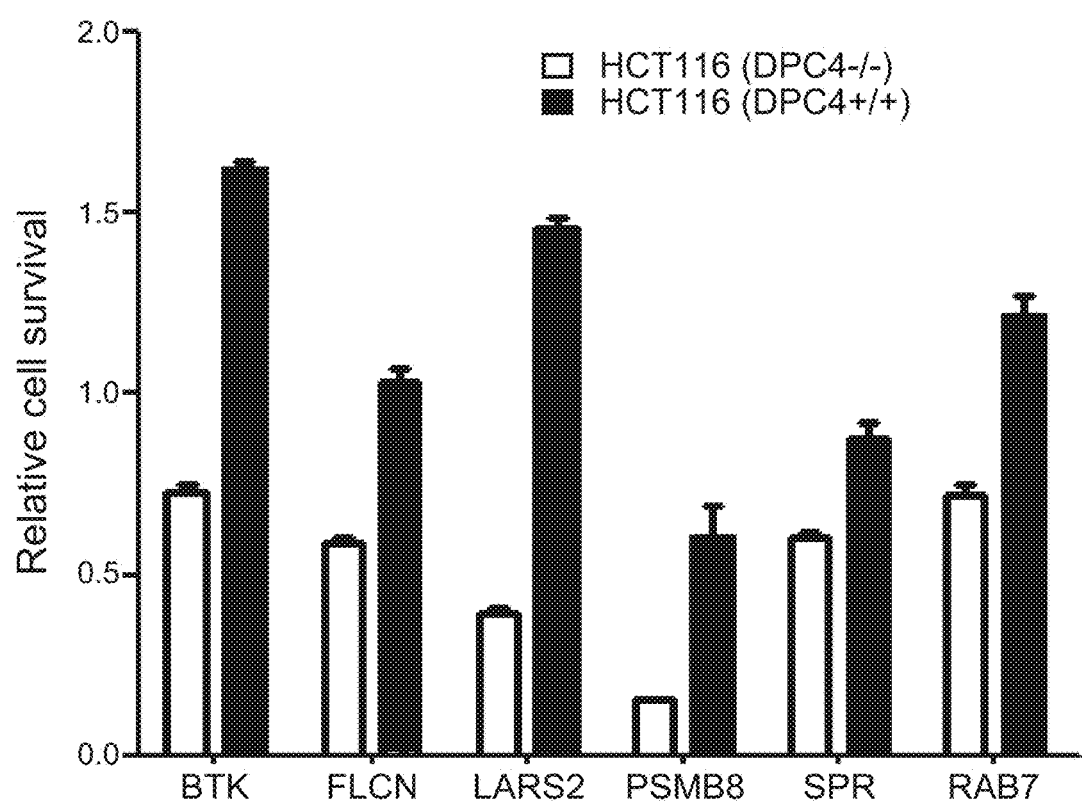
Figure 8:
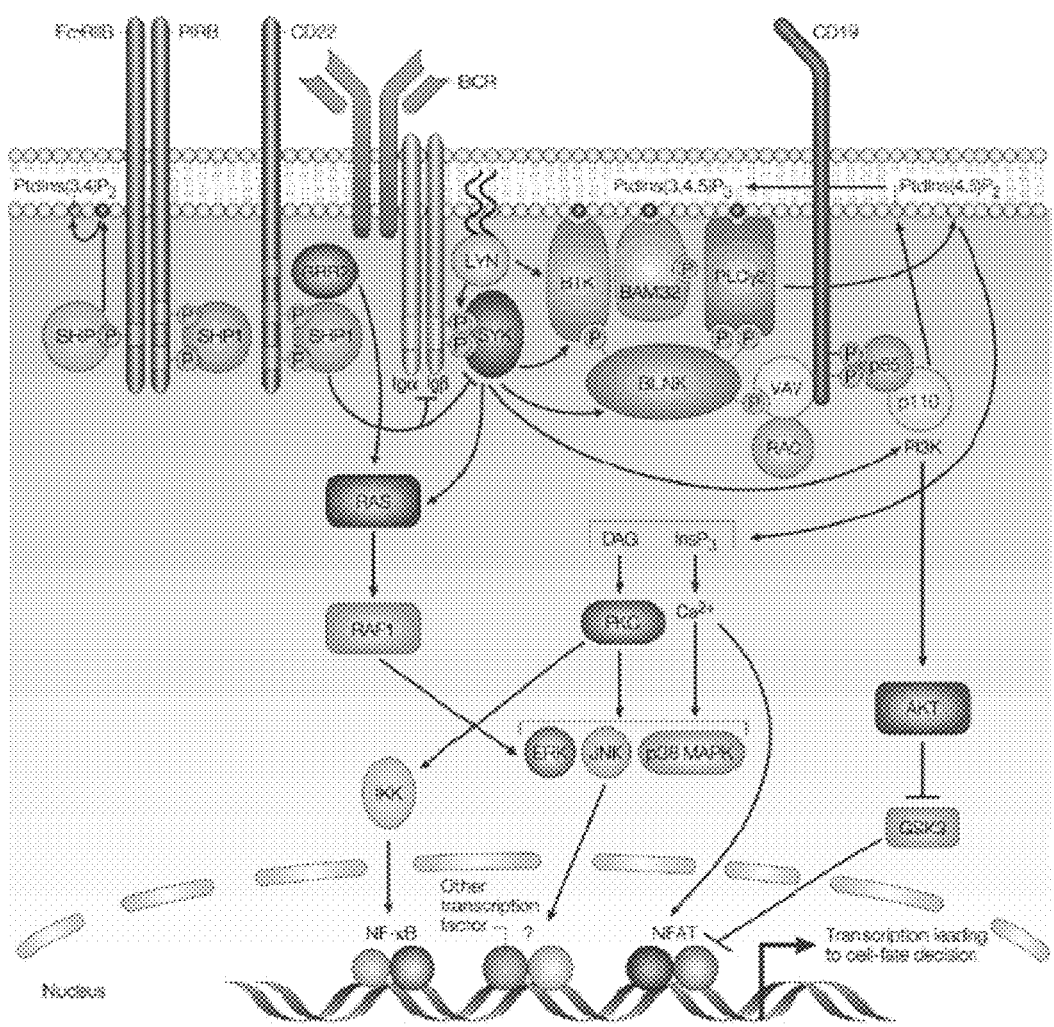
FIG. 8 depicts BTK and BCR-induced signaling pathways.

Bruton agammaglobulinemia tyrosinekinase (BTK) is a member of the Tec family, which includes kinases necessary for activation, growth, and differentiation of myeloid, mast, and B-cells. Activated BTK phosphorylates various signaling molecules in the PLC gamma, JNK, and p38 pathways. Mutations occurring in BTK result in X-linked agammaglobulinemia (XLA). Patients with XLA have normal pre-B cell populations in their bone marrow, but the cells fail to mature and enter into the blood circulation. FIG. 8 shows BTK and BCR-induced signaling pathways. (Niiro H & Clark E., *Nature Reviews Immunology* 945-956 (2002)). siRNA oligonucleotides targeting kinase genes selectively inhibit the growth of DPC4 null cancer cells in various cell line models. FIG. 1 depicts the workflow of the RNAi screen. FIG. 3B depicts potential synthetic lethal partners identified in the HCT 116 based isogenic cell lines. FIG. 3A depicts potential synthetic lethal partners identified in the pancreatic cell line models, BxPC-3 and PANC-1. Cell viability was determined by CellTiter-Glo 96 hrs after the initial reverse transfection in 384-well plates. SiRNA oligonucleotides targeting BTK gene selectively inhibit the growth of DPC4 null cancer cells in the cell line models. FIG. 2A depicts inhibition of growth of BxPC-3 based DPC4 null cell lines relative to DPC4 expressing lines by siRNA targeting BTK expression. FIG. 2B depicts inhibition of growth of HCT 116 based DPC4 null cell lines relative to DPC4 expressing lines by siRNA targeting BTK expression. Cell viability was determined by CellTiter-Glo 96 hrs after the initial reverse transfection in 384-well plates.

Figure 4:
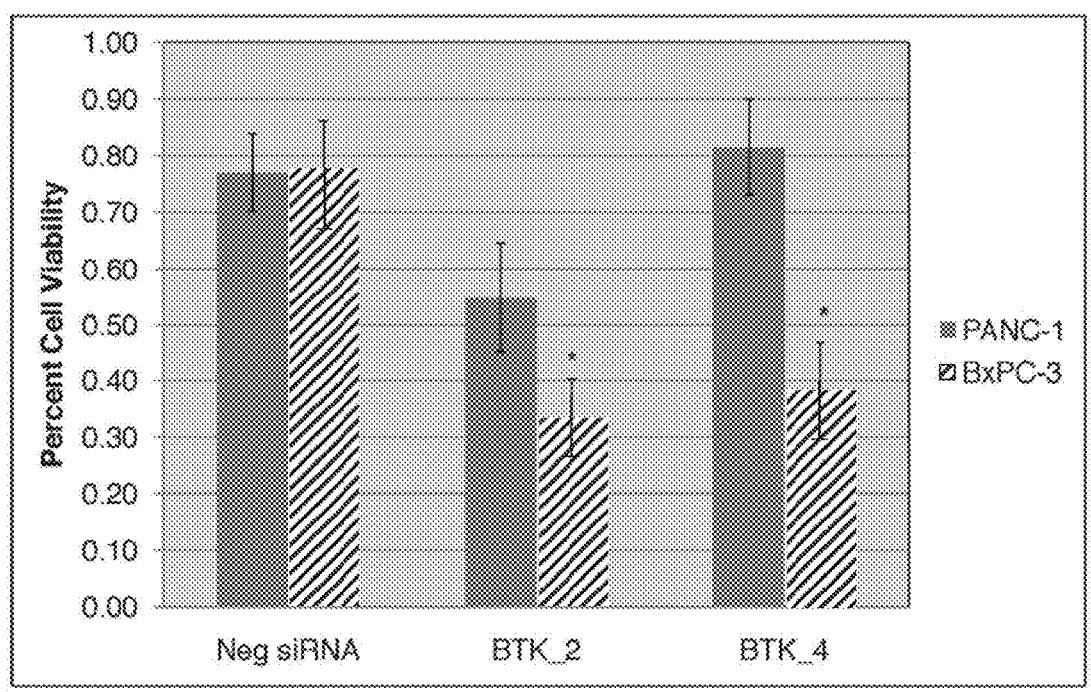
FIG. 4 depicts that BTK siRNA oligonucleotides selectively reduced the cell proliferation of BxPC-3 (DPC4-null) significantly relative to PANC-1 cells (DPC4-expressing).

FIG. 4 depicts that BTK siRNA oligonucleotides selectively reduces the cell proliferation of BxPC-3 (DPC4-null) significantly relative to PANC-1 cells (DPC4-expressing). Relative expression of BxPC-3 is significant [*p<0.05, Student's t-test] when compared to the mock-transfected Control (Neg siRNA). Normalization of relative expression was to the untreated cell control. Cell viability was determined through the CellTiter-Glo assay after 96 hours after initial transfection.

Figure 5A:
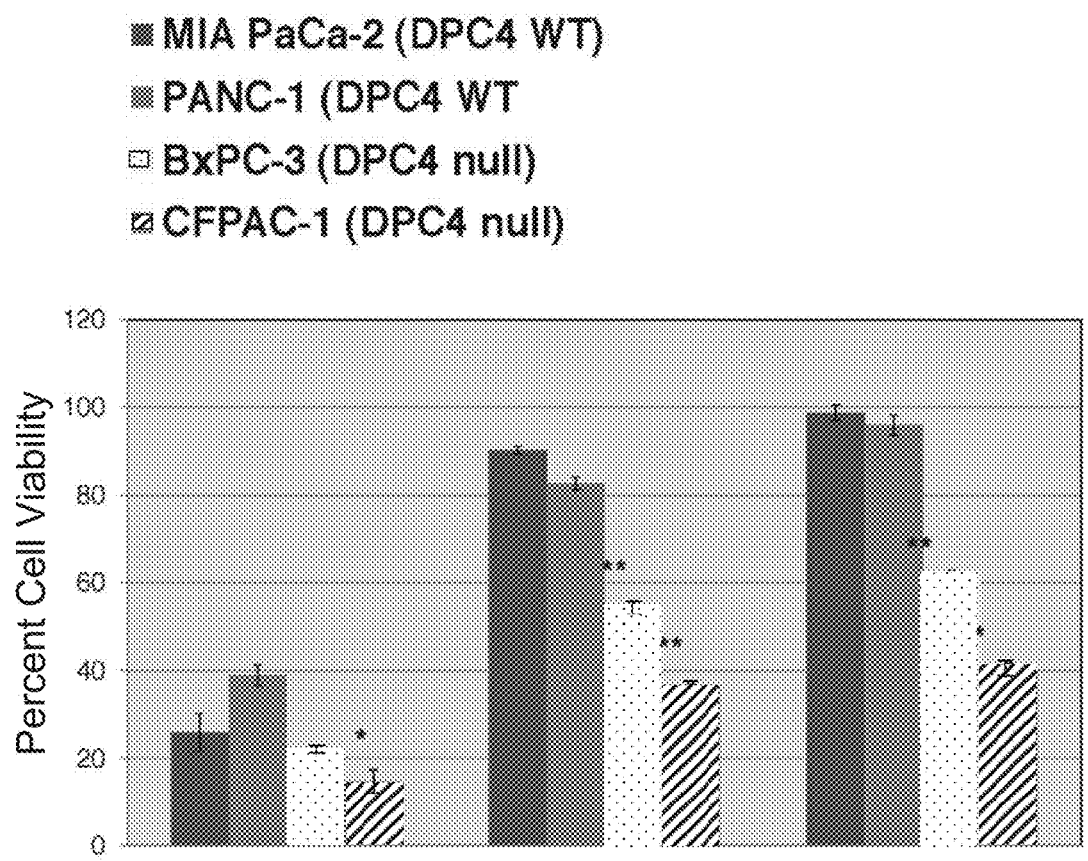
FIGS. 5A and 5B depict (FIG. 5A) that PCI-32765 inhibition of cell growth is DPC4 genotype selective and dose dependent in both the pancreatic and colon cancer cell line models.
Figure 5B:
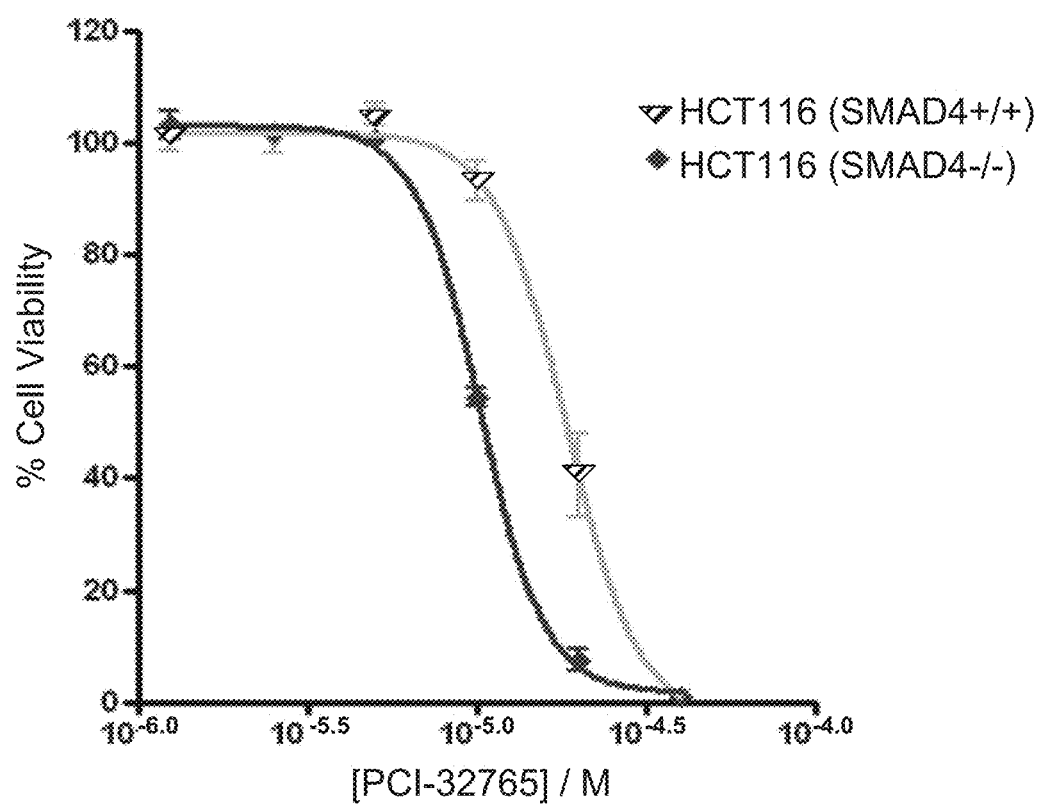
Figure 6:
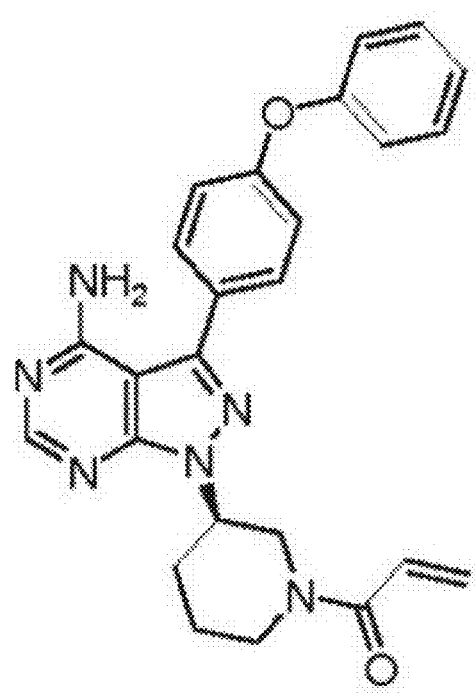
FIGS. 6 and 7 show different views of the chemical structure of PCI-32765.
Figure 7:
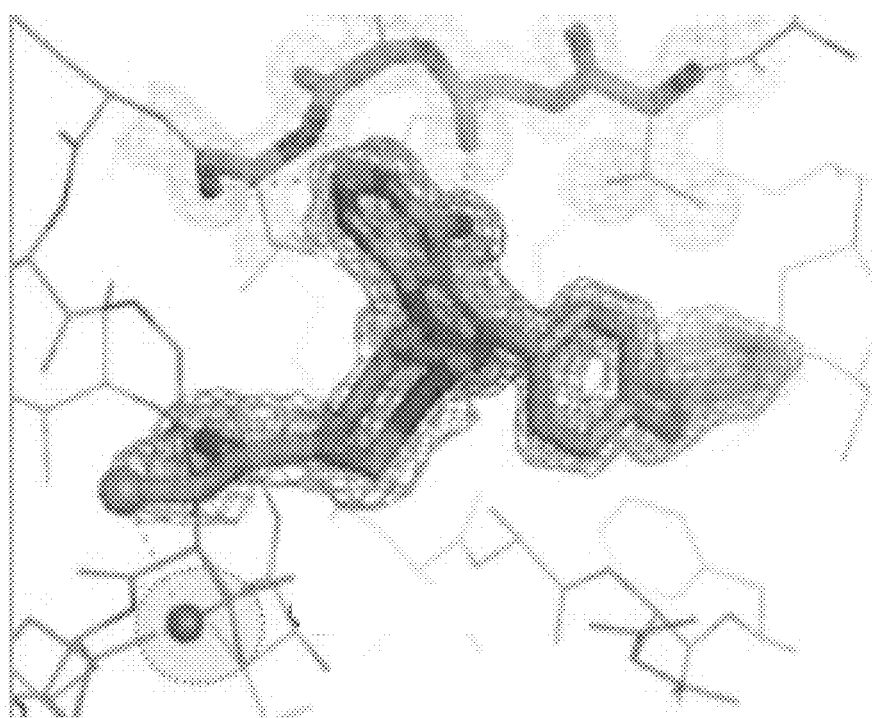

The activity of PCI-32765 is selective and dose dependent in the pancreatic and colon cancer cell line models. FIG. 5A shows that PCI-32765 has more activity in pancreatic cancer cell lines with a SMAD4/DPC4 deletion (BxPC-3 and CFPAC-1) [*p<0.05, **p<0.0001, Student's t-test] than in cell lines with SMAD4/DPC4 wildtype (MIAPaCa-2 and PANC-1). FIG. 5B shows that the selective activity of PCI-32765 was consistent in the isogenic DPC4 colon cancer cell lines, HCT116 and HCT116 DPC4(-). Cell viability was measured by Cell Titer-Glo after 96 hours of drug treatment. FIGS. 6 and 7 depict the chemical structure of PCI-32765.

BTK was identified as a potential synthetic lethal partner of the DPC4 gene in a RNAi screen using DPC4 isogenic cancer cell line models. The BTK siRNA selectivity findings were validated with a BTK small molecule inhibitor, PCI-32765, in our panel of pancreatic and colon isogenic cancer cell lines. Cell proliferation and viability was more diminished in the DPC4-mutated cell lines compared to DPC4-wildtype. A lower level of DPC4 protein expression in DPC4−/− lines was confirmed by western blotting.

Example 2

RNAi Screening and Genotype Specific Target Identification

A small interfering (siRNA) library based screening strategy to identify potential lethal targets against the deficiency of the DPC4 gene. The siRNA library is a kinase focused siRNA library that consisted of two siRNA oligonucleotides for each of the 624 protein kinase genes. A DPC4 isogenic pair of pancreatic cell lines, BxPC3-Vector and BxPC3-DPC4 were treated by the siRNA oligonucleotides in parallel and the effects of the siRNA oligonucleotides on the growth of the cell lines were then compared. siRNA oligonucleotides that selectively inhibited the cell growth of the BxPC3-Vector cell line were selected as potential positive hits. These gene target, once validated, represented potential drug targets that are very specific to cancer cells harboring mutations in the DPC4 gene. One of the top ranked hits identified from this screening is the Bruton's tyrosine kinase (BTK). The designed workflow of the target screening is depicted in FIG. 1.

Example 3

Figure 2C:
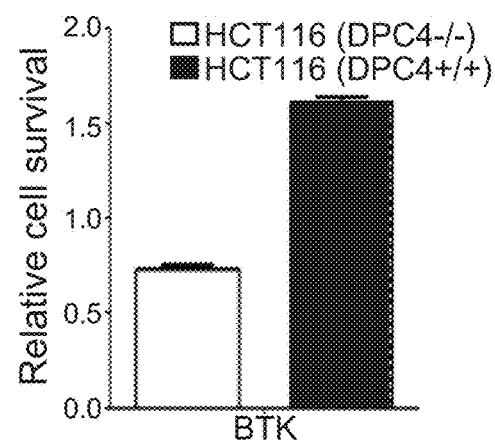

Selectivity of BTK siRNA Against DPC4 Null Cancer Cells in Various Cell Lines The selectivity was evaluated through Relative Cell Survival assay. The cells were treated with BTK or other candidates' siRNA oligos using a reverse transfection protocol in which the siRNA was pre-printed in 384-well plates and stored at −80° C. On the day of assay, transfection reagent and cells were added to the siRNA oligo sequentially and cells were allowed to grow for another 4 days. Cell viability was measured using the Cell-Titer Glo assay (Promega).

siRNA oligonucleotides targeting BTK gene selectively inhibit the growth of DPC4 null cancer cells were observed in three cell line models: BxPC-3 based DPC4 isogenic cell lines, with and without DPC4 deficiency, respectively (FIG. 2A), two different pancreatic cancer cell lines, BxPC-3 and PANC-1, with and without DPC4 deficiency, respectively (FIG. 2B), and a pair of DPC4 isogenic colon cancer cell lines, HCT-116 (DPC4 wildtype) and HCT-116-DPC4-knockout (FIG. 2C). DPC4 null, showed ~30% more cell growth inhibition than the BxPC3-DPC4 cells, which are DPC4 wildtype (FIG. 2A). Significantly more cell growth inhibition in BxPC-3 than in PANC-1 was shown in FIG. 2B. In colon cancer isogenic cells, BTK inhibition with DPC4 deficiency showed significantly more cell growth inhibition than that of BTK inhibition without DPC4 deficiency (FIG. 2C).

This selectivity of target siRNA against DPC4 null cells was further confirmed in a confirmation screen using two pancreatic cancer cell lines, BxPC3 and PANC-1, which are DPC4 null and DPC4 wildtype, respectively (FIG. 3A). The selectivity of other candidate targets such as FLCN, LARS2, PSMB8, SPR, and RAB7 were confirmed as well using BxPC3 and PANC-1 cell lines (FIG. 3A). The selectivity against the deficiency of DPC4 is significant in all candidates including BTK. BTK siRNA also showed significant selectivity against DPC4 deficiency in a pair of DPC4 isogenic colon cancer cell lines, HCT-116 and HCT-116-DPC4-knockout; so did other candidate targets such as FLCN, LARS2, PSMB8, SPR, and RAB7 (FIG. 3B). Further, significant selectivity against DPC4 deficiency was also observed between non-isogenetic cells that are with and without inactivated DPC4 gene.

Further, as shown in FIG. 4, BTK siRNA oligonucleotides selectively reduced the cell proliferation of BxPC-3 (DPC4-null) significantly relative to PANC-1 cells (DPC4-expressing). Relative expression of BTK in BxPC-3 with and without BTK siRNA treatment was significant [*$p<0.05$, Student's t-test] when compared to the mock-transfected Control (Neg siRNA). Normalization of relative expression was to the untreated cell control.

Example 4

BTK Inhibitor, PCI-32765, Selectively Inhibits Cell Growth in Cell Lines Harboring a DPC4 Mutation The inhibition of cancer cell growth by PCI-32765 is selective and dose dependent in both the pancreatic and colon cancer cell line models. PCI-32765 has more activity in pancreatic cancer cell lines with a DPC4 deletion (BxPC-3 and CFPAC-1) [*$p<0.05$, **$p<0.0001$, Student's t-test] than in cell lines with a DPC4 wildtype (MIA PaCa-2 and PANC-1) (FIG. 5A). The dose dependent selective activity of PCI-32765 was consistent in the isogenic DPC4/SMAD4 colon cancer cell lines, HCT116 and HCT116 DPC4(−) (FIG. 5B).

---

What is claimed is:

1. A method of treating a tumor in a human subject, the method comprising the steps of:

receiving a sample from the human subject, wherein the sample is selected from the group consisting of serum from the human subject and a cell from the human subject;

isolating RNA from the sample;

adding a reagent capable of specific binding to a marker consisting of SEQ ID NO: 1 (DPC4) to a mixture comprising the RNA;

adding a reverse transcriptase and subjecting the mixture to conditions that comprise allowing the formation of a DNA template comprising DPC4;

determining the DNA template comprises a DPC4 inactivation; and administering to the human subject a pharmaceutical composition comprising a therapeutically effective amount of a BTK inhibitor.

2. The method of claim 1, wherein the tumor arises from a cancer selected from the group consisting of pancreatic cancer, biliary tract cancers, neuroendocrine cancers, colorectal cancer, intramucosal carcinomas, invasive carcinomas without distant metastases, primary invasive carcinomas with distant metastases, and carcinomas metastasized to the human subject's liver or lymph nodes.

3. The method of claim 1, wherein the BTK inhibitor is PCI-32765.

4. The method of claim 1, wherein the pharmaceutical composition is orally or parenterally administered.

5. The method of claim 1, wherein the pharmaceutical composition comprises at least one carrier.

6. The method of claim 1 wherein the tumor arises from at least one of a pancreatic cancer and a colon cancer.

7. The method of claim 1, wherein determining the tumor in the human subject comprises the DPC4 inactivation further comprises determining the tumor comprises a DPC4 gene mutation.

8. The method of claim 1, wherein the sample comprises a pancreas biopsy from the human subject.

9. The method of claim 1, wherein the sample comprises a portion of a metastatic tumor from the human subject.

10. The method of claim 1, wherein the tumor arises from a colon cancer.

11. The method of claim 1, wherein the tumor arises from a pancreatic cancer.

12. The method of claim 1, further comprising determining the therapeutically effective amount of the BTK inhibitor based on DPC4 inactivation.

13. A method of treating a human subject with at least one of pancreatic cancer and colon cancer, the method comprising the steps of:
receiving a sample from the human subject, wherein the sample is selected from the group consisting of serum from the human subject and a cell from the human subject:
isolating RNA from the sample:
adding a reagent capable of specific binding to a marker consisting of SEP ID NO: 1 (DPC4) to a mixture comprising the RNA:
adding a reverse transcriptase and subjecting the mixture to conditions that comprise allowing the formation of a DNA template comprising DPC4;
determining the human subject exhibits an inactivation of a DPC4 gene; and
administering to the human subject a pharmaceutical composition comprising a therapeutically effective amount of a BTK inhibitor.

14. The method of claim 13, wherein the BTK inhibitor comprises PCI-32765.

15. The method of claim 13, wherein the pharmaceutical composition is orally or parenterally administered.

16. The method of claim 13, wherein the pharmaceutical composition comprises at least one carrier.

17. The method of claim 13, wherein determining the human subject exhibits the inactivation of the DPC4 gene further comprises determining an expression level of the DPC4 gene is reduced relative to a control sample.

18. The method of claim 13, wherein determining the human subject exhibits the inactivation of the DPC4 gene further comprises determining the subject comprises a mutation of the DPC4 gene.

19. The method of claim 13, wherein the human subject has colon cancer.

20. A method of treating a tumor in a subject, comprising:
receiving a sample from the subject;
isolating RNA from the sample;
adding a reagent capable of specific binding to a marker consisting of SEQ ID NO: 1 (DPC4) to the RNA;
adding a reverse transcriptase and allowing the formation of a DNA template comprising DPC4;
determining the DNA template comprises a DPC4 inactivation; and
administering to the subject a pharmaceutical composition comprising a therapeutically effective amount of a BTK inhibitor.

* * * * *